(12) United States Patent
O'Neill et al.

(10) Patent No.: US 8,933,011 B2
(45) Date of Patent: Jan. 13, 2015

(54) TREATMENT OF PRETERM LABOR WITH TOLL-LIKE RECEPTOR 9 ANTAGONISTS

(75) Inventors: Luke Anthony O'Neill, Dublin (IE); John O'Leary, Dublin (IE); Sean Daly, Dublin (IE); Andrea Scharfe Nugent, Dublin (IE)

(73) Assignees: The Provost, Fellows and Scholars of the College of the Holy and Undivided Trinity of Queen Elizabeth Near Dublin, Dublin (IE); The Coombe Lying-In Hospital, Dublin (IE)

( * ) Notice: Subject to any disclaimer, the term of this patent is extended or adjusted under 35 U.S.C. 154(b) by 462 days.

(21) Appl. No.: 13/120,605

(22) PCT Filed: Sep. 24, 2009

(86) PCT No.: PCT/EP2009/062395
§ 371 (c)(1),
(2), (4) Date: Jun. 8, 2011

(87) PCT Pub. No.: WO2010/034779
PCT Pub. Date: Apr. 1, 2010

(65) Prior Publication Data
US 2011/0236392 A1     Sep. 29, 2011

(30) Foreign Application Priority Data

Sep. 24, 2008 (IE) .................................... 2008/0773

(51) Int. Cl.
*A61K 31/37* (2006.01)
*A61K 45/06* (2006.01)
*A61K 39/395* (2006.01)
*A61K 31/47* (2006.01)
*A61K 31/00* (2006.01)
*A61K 31/7088* (2006.01)
*A61K 38/17* (2006.01)
*C12N 15/117* (2010.01)

(52) U.S. Cl.
CPC ................. *A61K 31/47* (2013.01); *A61K 31/00* (2013.01); *A61K 31/7088* (2013.01); *A61K 38/177* (2013.01); *A61K 45/06* (2013.01); *C12N 15/117* (2013.01); *C12N 2310/17* (2013.01)
USPC .......... 514/1; 514/12.1; 514/12.2; 424/130.1; 424/278.1; 424/697

(58) Field of Classification Search
None
See application file for complete search history.

(56) References Cited

U.S. PATENT DOCUMENTS

| 4,816,397 A | 3/1989 | Boss et al. |
| 4,816,567 A | 3/1989 | Cabilly et al. |
| 5,585,089 A | 12/1996 | Queen et al. |

FOREIGN PATENT DOCUMENTS

| EP | 0120694 A2 | 10/1984 |
| EP | 0125023 A1 | 11/1984 |
| EP | 0184187 A2 | 6/1986 |
| EP | 0239400 A2 | 9/1987 |
| EP | 0368684 A1 | 5/1990 |
| EP | 0623679 A1 | 11/1994 |
| GB | 2188638 A | 10/1987 |
| WO | WO-2006/010628 A1 | 2/2006 |
| WO | WO-2006/094124 A2 | 9/2006 |
| WO | WO-2008/076804 A2 | 6/2008 |
| WO | WO-2008/096122 A2 | 8/2008 |
| WO | WO-2008/114237 A2 | 9/2008 |

OTHER PUBLICATIONS

Denoeud et al., Malaria Journal 2007, 6:27 doi:10.1186/1475-2875-6-27.*
Scharfe-Nugent et al., J Immunol 2012; 188: 5706-57.*
Phillips, A., J Pharm Pharmacology, 2001; 53: 1169-1174.*
Vidal et al., European Journal of Cancer, 2005; 41: 2812-2818.*
Pirollo et al., Cancer Res. 2008; 68(5): 1247-1250.*
Winkler, Ther. Deliv. 2013; 4: 791-809.*
Steketee et al., Am J Trop Med Hyg., 2001; 64: 28-35.*
Mahmood, S., et al., "56 Aacetaminophen Hepatotoxicity is Dependent on TLR9 and Can Be Reduced by a TLR9 Antagonist", Gastroenterology, Elsevier, Philadelphia, PA LNKD—DOI:10.1016/S0016-5085(O8) 63514-3, vol. 134, No. 4, Apr. 1, 2008, pp. A-752.
Stoltner, Anton, "International Search Report", for PCT/EP2009/062395 as mailed Jul. 8, 2010, 5 pages.
Leung, T., et al., "Maternal plasma fetal DNA as a marker for preterm labour", Lancet (1998) 352, 1904-1905.
Chi, Hongbo, et al., "Innate recognition of non-self nucleic acids", Genome Biology 2008, vol. 9, Issue 3, Article 211, 7 pages.
Kramer, Boris W., et al., "Intra-amniotic LPS modulation of TLR signaling in lung and blood monocytes of fetal sheep", Innate Immunity 2009, htt;://ini.sagepub.com, 8 pages.
Lo, Dennis, et al., "Presence of fetal DNA in maternal plasma and serum", The Lancet, vol. 350, Aug. 16, 1997, pp. 485-487.
Ballantyne, Coco, "Mystery of preterm birth prompts search for better models", Nature Medicine, vol. 14, No. 8, Aug. 2008, p. 793.
Thomson, Andrew J., et al., "Low-molecular-weight heparin for immediate management of thromboembolic disease in pregnancy", The Lancet, vol. 352, Dec. 12, 1998, pp. 1904-1905.
Chn, Lisa Y. S., et al., "Serial Analysis of Fetal DNA Concentrations in Maternal Plasma in Late Pregnancy", Technical Briefs, Clinical Chemistry 49, No. 4, 2003, pp. 678-680.

* cited by examiner

*Primary Examiner* — Christina Borgeest
(74) *Attorney, Agent, or Firm* — Winstead PC

(57) ABSTRACT

The invention provides a method for treating or preventing preterm labor in pregnant female subjects. The method comprises the step of administering a therapeutically effective amount of a Toll-like Receptor 9 antagonist sufficient to prevent the activation of Toll-like Receptor 9 by fetal DNA. The invention further provides compositions comprising a Toll-like Receptor 9 antagonist for use in the methods of the invention. The compositions and methods of the present invention enhance gestation and therefore improve neonatal morbidity and mortality.

5 Claims, 16 Drawing Sheets

FDNA

0    5    15    30    60

B-Actin

0    5    15    30    60

CpG 0   5   15   30   60

B-Actin 0   5   15   30   60

Adult DNA 0   5   15   30   60

B-Actin 0   5   15   30   60

FDNA 0   5   15   30

B-Actin 0   5   15   30

Adult DNA 0   5   15

B-Actin 0   5   15

FDNA 0  5  15  30

B-Actin 0  5  15  30 a.

0   5   15  30  60    0   5   15  30  60
+ODN                  -ODN

Bactin 0   5   15  30  60    0   5   15  30  60 b.

0   5   15  30  60    0   5   15  30  60
+ chloroquin          -chloroquine

Bactin 0   5   15  30  60    0   5   15  30  60

A 0    5    15    30    60

B 0    5    15    30    60

TREATMENT OF PRETERM LABOR WITH TOLL-LIKE RECEPTOR 9 ANTAGONISTS

FIELD OF THE INVENTION

The present invention provides compositions and methods for the prevention of preterm labor. In particular, the present invention provides agents which inhibit a pro-inflammatory immune response which results from fetal DNA which is present in the maternal circulation binding to Toll-like Receptor 9. The invention further extends to the use of compounds which act as Toll-like Receptor 9 antagonists for the prevention of preterm labor.

BACKGROUND TO THE INVENTION

Preterm delivery (PTD) is defined as the delivery of a fetus after 20 weeks and before 37 completed weeks of gestation. Although the rate of pre term delivery varies from 7-10% worldwide, it is the single largest contributor to perinatal mortality in the developed world. North American studies confirm that infants born before 32 weeks gestation account for approximately 70% of infant mortality rates. It follows that if the number of preterm births were to decrease so would the perinatal mortality rate. However, despite extensive research in this area, the preterm delivery rate has remained stagnant. In the USA, it has even increased from 7-10% in 1990s to a record high of 12.9% in 2007.

Risk factors for early delivery include: infection, poor nutritional status, extremes of reproductive age, trauma, substance abuse and short interval between pregnancies. However, even when these risk factors are avoided, preterm delivery may occur. The single most significant risk for preterm delivery is a prior preterm birth. Preterm Delivery is usually preceded by preterm labor (PTL). Much research has been performed concerning the aetiology of preterm labor, but the exact cause remains unclear.

Clinical therapeutic approaches designed to prevent preterm labor are very limited. In 1998, maternal plasma fetal DNA was shown to be a marker for preterm labor (Leung T et al (1998) Lancet 352, 1904-1905). Although DNA is known to be a potent activator of the innate immune system, such activation is typically observed from microbial DNA, that is, DNA which is derived from a bacterial or viral source.

Toll-like Receptors (TLRs) form a family of pattern recognition receptors which have a key role in activating the innate immune response. Eleven Toll-like Receptors have been identified in humans to date. The members of the Toll-like Receptor family are highly conserved, with most mammalian species having between 10 to 15 Toll-like Receptors. Each Toll-like Receptor recognises specific pathogen-associated molecular signatures. Toll-like Receptor 9 (TLR9, TLR-9) senses CpG motifs in DNA. These are more common in bacterial and viral DNA and TLR9 has been shown to have an important role in the sensing of various pathogens during host defence.

The onset of preterm labor is typically treated using tocolytic therapies involving beta2 adrenergic receptor agonists. However, the administration of such beta2 adrenergic receptor agonists can lead to the occurrence of undesirable side effects, such as heart palpitations. There is therefore a need for improved therapeutic treatments for preterm labor.

SUMMARY OF THE INVENTION

Following extensive experimentation, the inventors have surprisingly identified for the first time, a biological mechanism which results in preterm labor. Specifically, the inventors have identified that fetal DNA can mediate a pro-inflammatory response in the pregnant mother during pregnancy. In particular, the inventors have identified that fetal DNA, which can be present in the maternal circulation, is a potent activator of a pro-inflammatory immune responses. The inventors have further identified that this pro-inflammatory response is mediated by fetal DNA binding to and activating Toll-like Receptor 9 (TLR9, TLR-9). In turn, the activated Toll-like Receptor 9 mediates a downstream signalling cascade which can be characterised as mediating activities such as (i) I-kappaB degradation, (ii) p38 MAP kinase activation and (iii) the induction of the pro-inflammatory cytokines, such as IL-6.

The inventors have therefore recognised that agents which inhibit activation of the Toll-like Receptor 9 by fetal DNA, which block the intracellular signalling mediated by Toll-like Receptor 9 following fetal DNA mediated activation, or which block Toll-like Receptor 9 mediated activation of the innate immune response, for example by inhibiting the pro-inflammatory immune response can be used to provide a novel clinical treatment for the prevention of the onset of preterm labor during pregnancy or for the prevention of premature labor.

Although Toll-like Receptor 9 has an accepted role in the detection of microbial DNA, the observation that fetal DNA binds to TLR9 and induces a pro-inflammatory response is entirely unexpected. In particular, it was extremely unexpected to identify that host DNA on its own could be bound by Toll-like Receptor 9 as it had been previously assumed that the primary role of TLR9 was in the detection of microbial DNA, such as double stranded DNA (dsDNA) derived from bacteria and viruses. Furthermore, even after identifying that the presence of fetal DNA in the maternal circulation mediated a pro-inflammatory response, it was not obvious as to how such an inflammatory response was mediated. In particular, aside from the understanding that TLR9 was specific only for microbial DNA, other receptors which had utility in sensing DNA were known, such as NALP3/cropyrin, the RIG-1-like receptor DAI and Pol III (DNA-dependent RNA polymerase III), however a role for those receptors in binding fetal DNA and mediating a pro-inflammatory immune response had not been suggested. Accordingly, the observed finding by the inventors that fetal DNA mediates a pro-inflammatory response in the mother and that this pro-inflammatory response is mediated, at least in part, by fetal DNA induced Toll-like Receptor 9 activation, is entirely unexpected and without precedent.

Accordingly, a first aspect of the present invention provides a method for treating or preventing the onset of premature labor and/or preterm birth, the method comprising the steps of:

providing a therapeutically effective amount of an agent which antagonises Toll-like Receptor 9 biological activity, and administering the same to a pregnant female subject in need of such treatment.

Typically the pregnant female subject has, or is at risk of having, preterm labor or giving birth to a preterm neonate. In certain embodiments, the determination as to whether the pregnant female subject is at risk of preterm labor, or presents with preterm labor is made by determining whether the level of a biological marker (biomarker) indicative of preterm labor is detected. In certain embodiments, the biomarker is the presence of fetal DNA in the serum of the maternal circulation. The person skilled in the art will be well aware of suitable methods for the detection of such a biomarker, for example by using any suitable real time PCR-based amplification technique, or the like. In certain embodiments the biomarker which is used to determine the occurrence or propensity for the development of preterm labor is a marker where the expression of that marker in the sample derived from the pregnant female subject is compared to a "reference expression profile" or "predetermined standard expression profile", these being a criterion expression values obtained from a pregnant female subject who is not at risk of preterm labor to which measured values from a pregnant female subject are compared in order to determine the pregnant female subject is at risk of developing preterm labor.

In embodiments where the biomarker being detected in the pregnant female subject is fetal DNA, the determination as to whether preterm labor may occur can be based on the presence or absence of fetal DNA in a biological sample, such as a whole blood or blood serum sample. Alternatively, the determination could be based on the presence of fetal DNA in a sample being in excess of a predetermined concentration, or present in an increased amount over that present in a previous sample derived from the same female subject. Alternatively, raised fetal DNA concentrations which are present in maternal plasma may provide a biomarker of the occurrence of preterm labor.

The occurrence of preterm labor may also be characterised by the occurrence of contractions and associated changes in the cervix, most typically the shortening or effacing of the cervix. In instances where contractions only are observed, that is, where there are no associated changes in the cervix, then this condition may be defined as threatened preterm labor. Threatened preterm labor may be treated using the composition and methods of the present invention in the manner described herein.

In certain embodiments, the agent is administered to a pregnant female subject from about week 18 of gestation to about week 37 of gestation.

In certain embodiments the Toll-like Receptor 9 antagonist is selected from the group comprising, but not limited to: an oligonucleotide, a oligodinucleotide, a nucleic acid, a small molecule, a protein, an antibody, an antibody binding fragment, a peptide, a peptidomimetic, a carbohydrate, a lipid, and a small molecule compound.

In a preferred embodiment, the Toll-like Receptor 9 antagonist is an oligonucleotide (DNA sequence, nucleic acid), an oligodinucleotide (ODN), or a CpG dinucleotide. Examples of oligonucleotides oligodinucleotides that antagonise the biological function (i.e. activation and signalling) of Toll-like Receptor 9 are known in the field. Such DNA sequences may, for example, comprise stimulatory CpG dinucleotides.

In certain embodiments the nucleic acid is a CpG-containing oligonucleotide and/or an oligonucleotide multimer, a synthetic oligonucleotide, an oligonucleotide analogue, or a CpG containing dinucleotide. In certain embodiments, the sequence of the oligonucleotide (a polynucleoside formed from a plurality of linked nucleoside units) is at least partially self-complementary, and may be from about 2 to about 50 nucleotides in length, but is typically about 11 nucleotides in length. Furthermore, such oligonucleotides can include naturally occurring nucleosides, modified nucleosides, or mixtures thereof.

Examples of such inhibitory oligonucleotide sequences are (TTAGGG)4 found in mammalian telomeres (InvivoGen) and the oligodinucleotide ODN 2088 which is derived from a murine stimulatory CpG ODN by the replacement of 3 bases (InvivoGen). Accordingly, in certain further embodiments, the Toll-like Receptor 9 antagonist is the oligonucleotide ODN2088. In certain embodiments, the Toll-like Receptor 9 antagonist is the CpG TLR9 antagonist dSLIM (double stem loop immunomodulator) (Mologen, Berlin, Germany). In certain further embodiments, the TLR9 antagonist is inhibitory CpG DNA (iCpG DNA). iCpG DNA has been shown to inhibit the TLR9 signalling pathway which is mediated by the adapter protein MyD88.

In certain embodiments the Toll-like Receptor 9 antagonist is an inhibitory nucleic acid which functions as an antagonist of TLR9 activation or expression, or which inhibits the expression of at least one nucleic acid which encodes for the TLR9 protein. In certain embodiments the TLR9 antagonist is selected from the group comprising, but not limited to: anti-sense oligonucleotides, triple helix molecules, anti-sense DNA, anti-sense RNA, ribozyme, iRNA, miRNA, sRNA, shRNA molecule. In certain embodiments, the short hairpin RNAs (shRNAs) functionally silence TLR9 and TLR9-related genes.

In certain embodiments, the Toll-like Receptor 9 antagonist is a small molecule. Typically said small molecule binds to the ligand binding site of Toll-like Receptor 9 in order to inhibit binding to Toll-like Receptor 9 of an activating, ligand, in this case fetal DNA. In certain embodiments the TLR9 antagonist is chloroquine (Aralen phosphate) or an analogue, pro-drug, derivative or metabolite thereof. In certain embodiments, the chloroquine metabolite is desethychloroquine.

Chloroquine is a drug from the 4-aminoquinolene family, having the structure N'-(7-chloroquinolin-4-yl)-N,N-diethyl-pentane-1,4-diamine.

In certain embodiments the TLR9 antagonist is an antibody molecule, or a binding fragment thereof. Typically the antibody has binding specificity to an epitope present on mammalian TLR9, typically human TLR9. In certain embodiments, the Toll-like Receptor 9 antagonistic monoclonal antibody IMG-305 (Immgenex).

In certain embodiments, more than one TLR9 antagonistic compound is administered to the cell, tissue or subject. For example, a TLR9 specific TLR9 antagonistic antibody may be administered to prevent the activation of TLR9, while an inhibitory nucleic acid may also be administered to inhibit the expression of TLR9. In certain embodiments, the antibody or antibody binding fragment may be administered within a liposome or related composition to facilitate delivery of the antibody into a cell, such that targeting of TLR9 within the endosomes of the cell can be effected.

In certain embodiments, the method further comprises the co-administration of at least one compound used in tocolytic therapy. Examples of compounds used in tocolytic therapy include, but are not limited to: ritodrine, terbutaline, hexoprenaline, magnesium sulphate, indomethacin and nifedipine. In certain further embodiments, the compound is a beta adrenergic drug.

In a further aspect, there is provided a Toll-like Receptor 9 antagonist agent for use in the prevention or treatment of the onset or premature labor and/or premature birth.

In a further aspect, there is provided the use of a Toll-like Receptor 9 antagonist agent in the preparation of a medicament for treating or preventing the onset of premature labor and or premature birth in a pregnant female subject.

A yet further aspect provides a pharmaceutical composition for use in the treatment or prevention of premature labor and or premature birth in a pregnant female subject comprising at least one Toll-like Receptor 9 antagonist agent along with at least one pharmaceutically acceptable diluent or carrier.

The inventors have identified that the present invention has utility in reducing neonatal morbidity and mortality by delaying delivery and allowing further fetal maturation.

Accordingly, the present invention provides a method for reducing neonatal morbidity or mortality by prolonging fetal gestation within an expectant mother, said method comprising the steps of:
  providing a therapeutically effective amount of Toll-like Receptor 9 antagonist agent, and
  administering the same to a pregnant female subject to enhance the term of fetal gestation.

A yet further aspect of the present invention provides a Toll-like Receptor 9 antagonist for use in enhancing the term of fetal gestation within an expectant mother.

A yet further aspect of the present invention provides the use of a Toll-like Receptor 9 antagonist in the preparation of a medicament for the enhancement of the term of fetal gestation in an expect mother in order to reduce the risk of neonatal mortality and morbidity.

A yet further aspect of the present invention provides a pharmaceutical composition for use in extending the term of fetal gestation comprising a Toll-like Receptor 9 antagonist and at least one pharmaceutically acceptable diluent and carrier.

A yet further aspect of the present invention provides a method of reducing one or more biological activities of Toll-like Receptor 9 (TLR9) in a Toll-like Receptor 9 expressing cell or tissue implicated in premature labor in a pregnant mammal, comprising:
  contacting the cell or tissue with at least one agent which functions as an antagonist of Toll-like Receptor 9 activity or expression, in an amount sufficient to reduce one or more biological activities of Toll-like Receptor 9.

As herein defined, the term "preterm labor" as used herein refers to a condition where labor begins more than three weeks before the full gestation period, which is typically 40 weeks. That is, preterm labor occurs at any stage prior to 37 weeks of gestation occurring. Preterm labor typically leads to the occurrence of labor, or physiological changes associated with labor in a pregnant female subject, if not treated. Preterm labor (preterm labor) may also be referred to as premature labor. The avoidance of preterm labor will prolong the term of pregnancy, which is also known as the gestation period, and therefore avoid preterm delivery and, in turn, reduce the risk of neonatal mortality and morbidity. As herein defined, the term "labor" (which may also be termed labor or birth) relates to the expulsion of the foetus and placenta from the uterus.

As herein defined, the term "a TLR9 expressing cell or tissue implicated in premature labor" means a cell or tissue which causes premature labor, or which secretes cytokines or other cellular mediators which cause premature labor to occur in a pregnant mammal. In certain embodiments, the Toll-like Receptor 9 expressing cell is an antigen presenting cell, such as a dendritic cell. The Toll-like Receptor 9 expressing cell may also be a B cell. Typically, Toll-like Receptor 9 expression is localised to intracellular compartments, such as endosomes. When bound by an activating ligand, such as CpG DNA, TLR9 recruits the adapter protein MyD88. The recruitment of MyD88 to the TIR domain of TLR9 initiates a signalling cascade which involved the interleukin-1 receptor associated kinases (IRAKs) and TRAF6. Activation of the transcription factor NF-kB and expression of pro-inflammatory cytokines, such as IL-6 and IL-8 can result. Inhibition or antagonism of TLR9 signalling can therefore target any step in the signalling cascade induced by TLR9 activation.

In certain embodiments the step of contacting the tissue and/or cell with the TLR9 antagonist occurs in a cell lysate, a reconstituted system or cells in culture. In certain embodiments the contacting step occurs on cells or a tissue present in a subject. In certain embodiments the TLR9 may be human TLR9 or any other mammalian TLR9.

In certain embodiments the method is performed on a pregnant mammal at risk of having premature labor.

According to a yet further aspect of the invention there is provided a method for the prevention of premature labor in a pregnant mammal, the method comprising the steps of:
  providing a therapeutically effective amount of an agent which modulates the function of Toll-like Receptor 9, and
  administering said compound to a subject in need of such treatment.

As herein defined, the term 'modulates the function' means that the agent changes or alters one or more of the biological functional activities of Toll-like Receptor 9. In certain embodiments, the modulation of Toll-like Receptor 9 function means that the agent inhibits the functional activation of Toll-like Receptor 9 following the binding of a TLR9 specific ligand and/or inhibits or suppresses the downstream intracellular signalling mediated by Toll-like Receptor 9 following activation by a TLR9 ligand, or the like. Modulation of the function of TLR9 may further extend to a suppression or inhibition of the expression of Toll-like Receptor 9 protein, or the inhibition or blocking of the expression of a gene which encodes Toll-like Receptor 9, hence, an agent which modulates TLR9 function may further inhibit the expression of the TLR9 protein, or block the expression of the TLR9 gene product.

As defined herein, an 'agent' which modulates TLR9 is a compound which suppresses or blocks the activation or function of Toll-like Receptor 9. The 'agent' may be an antagonist compound which inhibits or blocks the binding of a ligand or binding compound to Toll-like Receptor 9. For example, the 'agent' may be a Toll-like Receptor 9 binding agent which binds to the extracellular domain of Toll-like Receptor 9, said agent inhibiting the binding of activating ligands which have binding specificity for TLR9. Further, the 'agent' may be a compound which inhibits or suppresses intracellular signalling mediated by Toll-like Receptor 9 following ligand binding and/or Toll-like Receptor 9 activation. The 'agent' may further be a compound which modulates Toll-like Receptor 9 protein or gene expression, for example by inhibiting the expression of a gene encoding a Toll-like Receptor 9 protein. Such a compound may also be known as a TLR9 modulator agent.

In certain embodiments, the 'agent' which modulates TLR9 function may be a binding compound which has binding specificity or which specifically binds Toll-like Receptor 9. In certain embodiments, the binding compound may be selected from the group comprising, but not limited to: a CpG dinucleotide, an oligonucleotide, an oligodinucleotide, a small molecule, a protein, a peptide, a peptidomimetic, a nucleic acid, a polynucleotide, a polysaccharide, a carbohydrate, a lipid, an aptamer, and a naturally occurring compound, such as a plant derived compound or mimetic, analogue or derivative thereof.

In certain embodiments, the agent is a binding compound which binds to Toll-like Receptor 9 at a binding site other than the known TLR9 ligand binding site, and which, upon binding to TLR9, causes a change in the confirmation of Toll-like Receptor 9, which leads to an inhibition of Toll-like Receptor 9 activation and/or TLR9 agonistic ligand binding.

The term "specifically binds" or "binding specificity" refers to the ability of a TLR9 modulator agent or TLR9 binding compound to bind to a target epitope present on TLR9 with a greater affinity than it binds to a non-target epitope. In certain embodiments, specific binding refers to binding to a particular target epitope which is present on TLR9 with an affinity which is at least 10, 50, 100, 250, 500, or 1000 times greater than the affinity for a non-target epitope. In certain embodiments, binding affinity is determined by an affinity ELISA assay. In certain embodiments, affinity is determined by a BIAcore assay. In certain embodiments, binding affinity is determined by a kinetic method. In certain embodiments, affinity is determined by an equilibrium/solution method.

According to one embodiment, TLR9 modulators, including TLR9 binding agents, such as TLR9 antagonists, bind to TLR9 with high affinity, this being defined as a binding affinity which for example, has an affinity constant of at least about $10^7$ $M^{-1}$, typically about $10^8$ $M^{-1}$, and more typically, about $10^9$ $M^{-1}$ to $10^{10}$ $M^{-1}$ or stronger; and which modulates, e.g., reduces and/or inhibits, one or more TLR9 biological activities in a TLR9 responsive cell and/or tissue.

In certain embodiments, the TLR9 modulator agent is targeted to Toll-like Receptor 9 expressed on the cells or tissues which are likely mediate a pro-inflammatory response which is causative of premature labor. Such targeting may be by any suitable means known to the person skilled in the art, such as localised delivery, the use of a delivery vector, or a targeting means, such as an antibody which has binding specificity for a cell surface target expressed on the cell or tissue which is to be targeted. Examples of exemplary TLR9 activities that can be modulated, e.g., inhibited or reduced, using the methods and compositions of the invention include, but are not limited to, one or more of the following: (i) inhibiting or suppressing TLR9 expression, (ii) inhibiting TLR9 ligand binding and associated TLR9 activation, and (iii) inhibiting or suppressing intracellular signalling mediated by TLR9.

Accordingly, in a further aspect, the invention provides a method of modulating a function (e.g., altering one or more biological activities of TLR9) in a TLR9-responsive cell and/or tissue (e.g., a tissue which may mediate a pro-inflammatory response which is causative of premature labor). The method includes contacting the TLR9-responsive cell and/or TLR9-responsive tissue with a TLR9 modulator agent, e.g., a TLR9-binding agent, for example an antagonist of human TLR9 activity or expression, in an amount sufficient to modulate the function of the TLR9-responsive cell or tissue, or the biological activity of TLR9 in the cell or tissue. In one embodiment, the contacting step can be effected in vitro, for example in a cell lysate or in a reconstituted system. Alternatively, the subject method can be performed on cells in culture, e.g., in-vitro or ex-vivo. For example, cells, such as purified or recombinant cells, can be cultured in-vitro and the contacting step can be effected by adding the TLR9 modulator to the culture medium. Typically, the TLR9-responsive cell is a mammalian cell, such as a human cell. In some embodiments, the method can be performed on cells present in a subject, e.g., as part of an in-vivo protocol, or in an animal subject (including, e.g., a human subject, or an in-vivo animal model). For in vivo methods, the TLR9 modulator, alone or in combination with another agent, can be administered to a subject at risk of premature labor in an amount sufficient to modulate, one or more TLR9 mediated activities or functions in the subject. In some embodiments, the amount or dosage of the TLR9 modulator that is administered can be determined prior to administration by testing in-vitro or ex-vivo, the amount of TLR9 modulator required to alter, e.g., decrease or inhibit, one or more functional activity of TLR9, said functional activity typically being one or more TLR9 biological activities described herein.

In certain embodiments where inhibition, reduction or diminution of one or more biological activity of Toll-like Receptor 9 is desired, for example, Toll-like Receptor 9 activation or signalling, the TLR9-responsive cell and/or tissue is contacted with a TLR9 antagonist, e.g., by administering the TLR9 antagonist to the subject. In one embodiment, the TLR9 antagonist interacts with, e.g., binds to, a TLR9 polynucleotide or mRNA involved in the expression of the TLR9 protein, and reduces or inhibits one or more TLR9 activities. Typically, the TLR9 antagonized is a mammalian TLR9 (or a functional variant thereof), e.g., mammalian TLR9, typically human TLR9. In certain embodiments, the Toll-like Receptor 9 which has its function antagonized is human Toll-like Receptor 9, having the amino acid sequence as defined in SEQ ID NO:1:

```
SEQ ID NO: 1:
MGFCRSALHP LSLLVQAIML AMTLALGTLP AFLPCELQPH GLVNCNWLFL KSVPHFSMAA

PRGNVTSLSL SSNRIHHLHD SDFAHLPSLR HLNLKWNCPP VGLSPMHFPC HMTIEPSTFL

AVPTLEELNL SYNNIMTVPA LPKSLISLSL SHTNILMLDS ASLAGLHALR FLFMDGNCYY

KNPCRQALEV APGALLGLGS LTHLSLKYNN LTVVPRNLPS SLEYLLLSYN RIVKLAPEDL

ANLTALRVLD VGGNCRRCDH APNPCMECPR HFPQLHPDTF SHLSRLEGLV LKDSSLSWLN

ASWFRGLGNL RVLDLSENFL YKCITKTKAL QGLTQLRKLN LSFNYQKRVS FAHLSLAPSF

GSLVALKELD MHGIFFRSLD ETTLRPLARL PMLQTLRLQM NFINQAQLGI FRAFPGLRYV

DLSDNRISGA SELTATMGEA DGGEKVWLQP GDLAPAPVDT PSSEDFRPNC STLNFTLDLS

RNNLVTVQPE MFAQLSHLQC LRLSHNCISQ AVNGSQFLPL TGLQVLDLSH NKLDLYHEHS

FTELPRLEAL DLSYNSQPFG MQGVGHNFSF VAHLRTLRHL SLAHNNIHSQ VSQQLCSTSL

RALDFSGNAL GHMWAEGDLY LHFFQGLSGL IWLDLSQNRL HTLLPQTLRN LPKSLQVLRL

RDNYLAFFKW WSLHFLPKLE VLDLAGNQLK ALTNGSLPAG TRLRRLDVSC NSISFVAPGF

FSKAKELREL NLSANALKTV DHSWFGPLAS ALQILDVSAN PLHCACGAAF MDFLLEVQAA

VPGLPSRVKC GSPGQLQGLS IFAQDLRLCL DEALSWDCFA LSLLAVALGL GVPMLHHLCG
```

```
-continued
WDLWYCFHLC LAWLPWRGRQ SGRDEDALPY DAFVVFDKTQ SAVADWVYNE LRGQLEECRG

DRKDVVVLVI LSPDGRRSRY VRLRQRLCRQ SVLLWPHQPS GQRSFWAQLG MALTRDNHHF

YNRNFCQGPT AE
```

The human Toll-like Receptor 9 of SEQ ID NO:1 comprises 1032 amino acids, and is defined as the human Toll-like Receptor 9 sequence as defined as Genbank Accession Number AAQ89443 (URL www.ncbi.nlm.nih.gov)). The TLR9 sequence of SEQ ID NO:1 encodes a 1032 amino acid protein containing 27 N-terminal LRRs with a calculated molecular weight of 116 kDa. The gene for TLR9 has been mapped to human chromosome 3p21.3. TLR9 is most closely related to TLR7 and TLR8 with 36% and 35% overall amino acid sequence identity, respectively and thus along with TLR7 and TLR8 constitutes a new sub-family of the TLRs. In vivo, TLR9 mRNA is expressed in spleen, lymph node, bone marrow, and PBLs. TLR9 mRNA is expressed at the highest levels in B cells and dendritic cells (DC). TLR9 is expressed primarily on antigen presenting cells such as B cells and DC. In human DC, TLR9 is restricted to a subset of DC, plasmacytoid DC, responsible for production of high levels of type I IFN (IFN alpha). TLR9 recognizes synthetic CpG oligonucleotides and unmethylated CpG motifs in bacterial and viral DNA.

As herein defined, Toll-like Receptor 9 may be also referred to as CD289 (cluster of differentiation 289), TLR9 or TLR-9. Typically, the Toll-like Receptor 9 is human Toll-like Receptor 9. Alternatively, the Toll-like Receptor 9 is murine Toll-like Receptor 9. In further embodiments, the Toll-like Receptor 9 is a homologue or orthologue of human TLR9 which is derived from any mammal other than a human or mouse, for example, a cow or rat. In certain further embodiments, the agent which suppresses TLR9 function is cross-reactive, in that it mediates the suppression of Toll-like Receptor 9 function in Toll-like Receptor 9 derived from different species.

As herein defined, the term "Toll-like Receptor 9 activation" means the binding of Toll-like Receptor 9 by a ligand, wherein the ligand acts as an agonist and activates Toll-like Receptor 9 in order to induce an intracellular signalling cascade. Intracellular signalling mediated following Toll-like Receptor 9 activation and signalling results in the activation of transcription factors and the expression of genes which mediate a pro-inflammatory immune response.

In certain embodiments the TLR9 modulator agent inhibits the interaction between Toll-like Receptor 9 and a Toll-like Receptor 9 agonist ligand.

In certain embodiments, the TLR9 modulator agent that suppresses Toll-like Receptor 9 activation and/or signalling is a compound which acts as a Toll-like Receptor 9 antagonist. Typically, antagonism of Toll-like Receptor 9 function is achieved by the binding of the Toll-like Receptor 9 modulator agent to Toll-like Receptor 9 in such a way that ligand binding to Toll-like Receptor 9 is prevented. This inhibition of Toll-like Receptor 9 ligand binding may be achieved by a number of means, for example, through partially or fully blocking the Toll-like Receptor 9 ligand binding site, or by inducing a conformational change upon binding to or association with Toll-like Receptor 9 which results in the Toll-like Receptor 9 ligand binding site being altered in a manner which prevents Toll-like Receptor 9 ligand binding, for example due to a conformational change of the tertiary structure of the Toll-like Receptor 9 ligand binding site which prevents TLR9 ligand binding.

In certain embodiments, the TLR9 modulator agent binds to at least one epitope present on TLR9, wherein binding to this epitope results in an inhibition of TLR9 function, most typically TLR9 activation or TLR9 mediated downstream signalling. As herein defined, an "epitope" refers to a plurality of amino acid residues which encode for the TLR9 protein which are capable of being recognised by, and bound to by, a binding compound such as a ligand, small molecule, antibody or the like. Epitopes are generally comprised of chemically active surface groups and have specific three dimensional structural characteristics, as well as specific charge characteristics, the aforementioned contributing to the three dimensional structure of the epitope.

Typically, the TLR9 modulator agent antagonises the functional activity of TLR9 and as such binds to an epitope known as an inhibiting epitope or an inhibitory epitope. An "inhibiting" or "inhibitory" epitope means an epitope present on TLR9 that, when bound by a binding compound such as a small molecule or an antibody, results in the loss of biological activity of TLR9, for example due to the binding compound preventing the binding of TLR9 by a TLR9 agonist. The epitope that is present on TLR9, and which is bound by the binding compounds in order to antagonise TLR9 function, may comprise 5 or more amino acid residues.

In certain embodiments, the TLR9 modulator agents of the invention may recognise a continuous epitope. In further embodiments, the epitope is a discontinuous epitope comprising a non-continuous series of residues of the mature Toll-like Receptor 9 (TLR9) protein.

In certain embodiments the TLR9 modulatory agent is a soluble form of recombinant Toll-like Receptor 9. In particular the soluble form of TLR9 is a fusion protein substantially comprising a portion of the extracellular domain on the TLR9 protein conjoined to a secondary protein. In certain embodiments, the secondary protein may be an Fc domain of an antibody, or a fragment thereof.

In certain further embodiments, the TLR9 modulatory agent is an inhibitory nucleic acid which inhibits expression of the TLR9 protein, or a protein involved in TLR9 mediated intracellular signalling and activation of the immune system. In certain embodiments the inhibitory nucleic acid protein is selected from the group consisting of: anti-sense oligonucleotides, triple helix molecules, anti-sense DNA, anti-sense RNA, ribozyme, iRNA, miRNA, sRNA, and shRNA. In certain embodiments, the short hairpin RNAs (shRNAs) functionally silence TLR9 and TLR9-related genes. In certain embodiments the nucleic acid is a CpG-containing oligonucleotide and/or an oligonucleotide multimer, a synthetic oligonucleotide or an oligonucleotide analogue. In certain embodiments, the sequence of the oligonucleotide (a polynucleoside formed from a plurality of linked nucleoside units) is at least partially self-complementary, and may be from about 2 to about 50 nucleotides in length, but is typically about 11 nucleotides in length. Furthermore, such oligonucleotides can include naturally occurring nucleosides, modified nucleosides, or mixtures thereof. In certain embodiments the TLR9 antagonist is IMO-3100 (Idera Pharmaceuticals). In certain further embodiments the TLR9 antagonist is DV056 a 25 base, single stranded phosphorothioate oligodeoxynucleotide.

In certain embodiments, the methods of the invention are used to administer a therapeutically effective amount of a TLR9 modulator agent to a subject in need of such treatment in order to reduce or inhibit one or more TLR9 biological activities in a TLR9 expressing cell or tissue of the myocardium, thereby preventing premature labor in a pregnant mammal.

According to a yet further aspect of the invention there is provided a pharmaceutical composition for use in the prevention of premature labor in a pregnant mammal, comprising an agent which modulates the function or expression of Toll-like Receptor 9 along with at least one pharmaceutically acceptable carrier, diluent, solubilizer, emulsifier, preservative and/or adjuvant.

In certain embodiments the TLR9 antagonist agent is a compound which is a TLR9 antagonist selected from the group consisting of: a polyclonal antibody, a monoclonal antibody, a humanized antibody, a chimeric antibody or antibody fragment, an aptamer, a fusion protein and a peptidomimetic.

In certain embodiments, the TLR9 antagonist agent is a soluble form of the TLR9 receptor. Said soluble form of TLR9 may be recombinant.

In certain embodiments the TLR9 antagonist agent is an inhibitory nucleic acid based compound which inhibits the expression of TLR9.

In certain embodiments, the pharmaceutical composition may further comprise a secondary therapeutic agent which is employed in tocolytic therapy, or which suppresses the pro-inflammatory immune response which is mediated by TLR9 activation. Such a secondary therapeutic compound may include, but is not limited to: an immune suppressor, which may be at least one of the group consisting of, but not limited to: a glucocorticoid, in particular a glucocorticoid which suppresses the expression of a cytokine; a cytostatic such as an alkylating agent, an anti-metabolite such as methotrexate; an antibody or related binding fragment, such as an anti-CD3 antibody such as OKT-3, an anti-CD20 antibody, the anti-TNF-alpha antibody infliximab (REMICADE™), etanercept (ENBREL™) or adalimumab (HUMIRA™); a drug compound which acts on immunophilins such as cyclosporine, tacrolimus or sirolimus; or a small molecule, such as FTY720 or a therapeutic cardiovascular compound comprising at least one or more of; an HMG-CoA reductase inhibitor, a vasodilatory agent, a diuretic, an angiotensin converting enzyme inhibitor, a beta-blocker, an angiotensin II receptor antagonist, a calcium channel blocker, an anticoagulant, an adenosine diphosphate receptor antagonist such as ticlopidine or clopidogrel bisulfate, a glycoprotein IIb/IIIa receptor antagonist such as bivalirudin, argatroban or heparin, a beta adrenergic receptor agonist, an antithrombolytic agent, an antioxidant, and an alpha blocker.

In certain embodiments, the Toll-like Receptor 9 antagonist agent is orally administered to the subject at a dose of from about 1 mg/kg to about 10 mg/kg of the subject's body weight per day. In certain embodiments, the dose of the Toll-like Receptor 9 modulator agent is from about 100 mg per day to about 1000 mg per day. In certain further embodiments, the dose of the Toll-like Receptor 9 modulator agent is from about 200 mg per day to about 300 mg per day.

In certain embodiments, the Toll-like Receptor 9 antagonist agent is administered to the subject parenterally with a dosage range of between about 0.001 mg/kg to 1.0 mg/kg of the mammal's body weight.

In certain embodiments, the Toll-like Receptor 9 antagonist agent is administered to the subject for a time, and under conditions sufficient to down regulate the level and/or activity of Toll-like Receptor 9.

In certain embodiments, the Toll-like Receptor 9 antagonist agent at least one aptamer with binding specificity to Toll-like Receptor 9, which causes blocking or suppression of the functional activity of Toll-like Receptor 9. Techniques for the selection of suitable aptamers will be well known to the person skilled in the art, for example, using SELEX technology.

Accordingly, in various further embodiments, the present invention extends to a method of identifying and isolating nucleic acid ligands which have binding specificity for Toll-like Receptor 9, the method comprising the steps of:
 (a) providing a candidate mixture of nucleic acids
 (b) contacting a cell expressing Toll-like Receptor 9 with the candidate nucleic acid mixture
 (c) selecting nucleic acids which have an increased affinity to Toll-like Receptor 9 relative to the other candidate nucleic acids,
 (d) amplifying the selected nucleic acids in order to provide at least one nucleic acid with affinity for Toll-like Receptor 9, and
 (e) selecting at least one nucleic acid therefrom which has a high affinity and specificity for Toll-like Receptor 9.

The inventors have further identified that suppression of the function of Toll-like Receptor 9 can be achieved by means of reducing the amount of fetal DNA ligand which is available to bind to and activate Toll-like Receptor 9. A reduction in the amount of ligand which is available to bind Toll-like Receptor 9 results in a downregulation of Toll-like Receptor 9 mediated signalling and thus of TLR9-mediated activation of the pro-inflammatory immune response. In particular, the inventors have identified the utility of a soluble peptide which is either a soluble form of Toll-like Receptor 9 or a functional fragment thereof in suppressing Toll-like Receptor 9 mediated activation of a pro-inflammatory response. This suppression results from the soluble form of Toll-like Receptor 9 or truncated form of Toll-like Receptor 9 competing with TLR9 for TLR9 specific binding ligands. This competitive binding results in the soluble or truncated forms of TLR9 effectively "mopping up" available Toll-like Receptor 9 fetal DNA ligand. An associated reduction in the binding and activation of membrane bound Toll-like Receptor 9 results in a down-regulation of the Toll-like Receptor 9 mediated pro-inflammatory immune response.

Accordingly, the administration of a soluble form of Toll-like Receptor 9 has utility in methods for suppressing the pro-inflammatory immune response which contributes to the occurrence of premature labor in a pregnant mammal.

Accordingly, a further aspect of the present invention provides a method for preventing premature labor in a pregnant mammal, the method comprising the steps of:
 providing a therapeutically effective amount of a soluble form of Toll-like Receptor 9 or a soluble fragment thereof which is capable of binding to a Toll-like Receptor 9 ligand, and
 administering a therapeutically effective amount of said compound to a subject in need of such treatment.

The present invention further extends to screening assays for use in identifying compounds which are capable of preventing premature labor in a pregnant mammal resulting from fetal DNA activation of TLR9, or by signalling through the fetal DNA activated TLR9 pathway, by means of suppressing the function of Toll-like Receptor 9.

A yet further aspect of the present invention provides a screening method for the identification of compounds which suppress fetal DNA mediated Toll-like Receptor 9 mediated inflammation and premature labor in a pregnant mammal, the method comprising:

providing Toll-like Receptor 9 receptor along with a fetal DNA ligand which has binding specificity thereto, bringing a candidate compound into contact with Toll-like Receptor 9, exposing Toll-like Receptor 9 to the Toll-like Receptor 9 fetal DNA ligand, determining the binding of the Toll-like Receptor 9 fetal DNA ligand to Toll-like Receptor 9, wherein the inhibition of binding of Toll-like Receptor 9 by the Toll-like Receptor 9 fetal DNA ligand indicates that said candidate compound is a modulator of Toll-like Receptor 9 activation and signalling.

A further aspect of the present invention provides a modulator agent identified according to the foregoing aspect of the invention for use in the prevention of premature labor of a pregnant mammal.

A yet further aspect of the present invention provides for the use of an agent which functions as an antagonist of TLR9 activity or expression in the preparation of a medicament for the prevention of premature labor in a pregnant mammal.

A yet further aspect of the invention provides an agent which functions as an antagonist of TLR9 activity or expression for use in the prevention of premature labor in a pregnant mammal.

In various further aspects, the present invention extends to compositions and methods for preventing preterm labor in a pregnant mammal, wherein such compositions and methods perform at least one of the following functions: (i) inhibition of activation of I-kappaB degradation, (ii) p38 MAP kinase activation, (iii) IL-6 cytokine production.

Accordingly, a yet further aspect of the present invention provides a method for the prevention of premature labor in a pregnant mammal, the method comprising the steps of:

providing a therapeutically effective amount of an agent which inhibits at least one of I-kappaB degradation, p38 MAP kinase activation or IL-6 production, in a manner sufficient to suppress a pro-inflammatory immune response which would have resulted if the I-kappaB degradation, p38 MAP kinase activation or IL-6 production had not be inhibited, and administering the same to a subject in need of such treatment.

In certain embodiments, the I-kappaB degradation, p38 MAP kinase activation or IL-6 production, which are inhibited by the agent are mediated following the activation of Toll-like Receptor 9 following binding by fetal DNA.

In certain further embodiments, the I-kappaB degradation, p38 MAP kinase activation or IL-6 production, which are inhibited by the agent are mediated following the activation of the Nalp3/cryopyrin or DAI receptors following binding by fetal DNA.

A yet further aspect of the invention provides the use of an agent which inhibits at least one of I-kappaB degradation, p38 MAP kinase activation or IL-6 production in the preparation of a medicament for the prevention of preterm labor in a pregnant mammal.

In certain embodiments, the I-kappaB degradation, p38 MAP kinase activation or IL-6 production, which are inhibited by the agent are mediated following the activation of Toll-like Receptor 9 following binding by fetal DNA.

In certain further embodiments, the I-kappaB degradation, p38 MAP kinase activation or IL-6 production, which are inhibited by the agent are mediated following the activation of the Nalp3/cryopyrin or DAI receptors following binding by fetal DNA.

A still further aspect of the present invention provides an agent which inhibits at least one of I-kappaB degradation, p38 MAP kinase activation or IL-6 production for use in the prevention of preterm labor in a pregnant mammal.

BRIEF DESCRIPTION OF THE FIGURES

The present invention will now be described with reference to the following examples which are provided for the purpose of illustration and are not intended to be construed as being limiting on the present invention wherein:

FIG. 3 shows that fetal DNA induces 1-kappaB degradation in Peripheral blood mononuclear cells.

FIG. 4 shows fetal DNA administered in a dose-dependent manner induces 1 kB degradation.

FIG. 7A shows that adult DNA from the peripheral blood of a female subject does not result in IkB degradation when used to stimulate Namalwa cells, when performed in a time course in minutes (FIG. 7A). FIG. 7B shows a B-actin control for the same experiment.

DETAILED DESCRIPTION OF THE INVENTION

Figure 1:
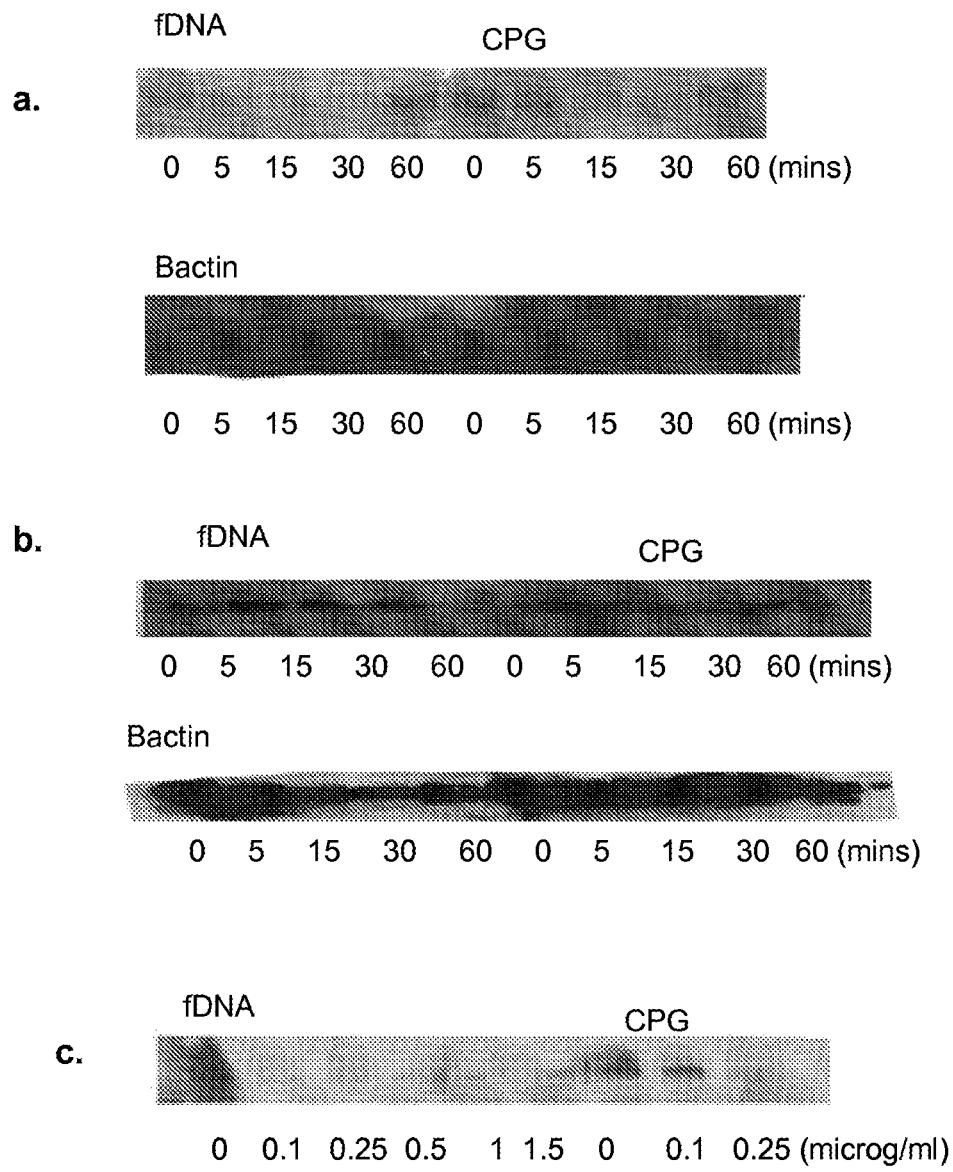
FIG. 1 shows that fetal DNA can (a) activate I-kappaB degradation in a time-course, (b) activate p38 MAP kinase, and (c) dose-dependently cause I-kappaB degradation. All of these responses are in the B cell line Namalwa, and the effect of fetal DNA is more potent than the TLR9 ligand agonist CpG DNA.

The inventors have surprisingly shown that fetal DNA acts as a potent activator of the pro-inflammatory immune response. This pro-inflammatory immune response is mediated by fetal DNA, which can be present in the maternal circulation, and which can bind to Toll-like Receptor 9 expressed by maternal cells, such as Toll-like Receptor 9 expressing antigen presenting cells. The activation of Toll-like Receptor 9 results in a pro-inflammatory immune response which can induce preterm labor and, in turn preterm birth. The preterm birth of a neonatal can pose significant health risks to the neonatal and is associated with a significantly enhanced rate of morality and morbidity.

The inventors have shown that the binding of fetal DNA to Toll-like Receptor 9 results in an immune response which is mediated by pro-inflammatory mediators and signalling pathways such as that resulting from the activation of I-kappaB degradation, p38 MAP kinase activation and also induction of the pro-inflammatory cytokine IL-6.

Inflammation and inflammation-associated molecules are associated with the process of normal labor at full term. Specifically, labor onset results in the recruitment of neutrophils, macrophages and T-lymphocytes to the myometrium. An increase in IL-1, IL-6, IL-8 and TNF-alpha is also seen in the laboring uterus and cervix. These pro-inflammatory cytokines are understood to contribute to labor by stimulating IL-8 and prostaglandin production, this causing myometrial contraction.

Accordingly, without wishing to be bound by theory, the inventors predict that fetal DNA mediated TLR9 activation results in the stimulation or an upregulation of an immune response which may induce labor through the above described immunomodulatory mechanisms (i.e. an inflammatory response, which results in labor behaviour in myometrium, cervix, uterus by creating the immune conditions which could otherwise not be seen until labor at full term).

The inventors have therefore identified the utility of Toll-like Receptor 9 antagonist compounds in inhibiting Toll-like Receptor 9 activation by fetal DNA, and in turn, the development of a pro-inflammatory immune response which results from the observed fetal DNA Toll-like Receptor 9 activation. The down-regulation or suppression of the Toll-like Receptor 9 mediated immune response in turn prevents the occurrence of, or severity of preterm labor. This therefore reduced the incidence of premature birth resulting from premature labor.

The finding that fetal DNA mediates a pro-inflammatory immune response in the pregnant female subject has led the inventors to identify that other DNA receptors, in addition to Toll-like Receptor 9, may also play a role in mediating the pro-inflammatory immune response which has been identified as being causative of premature labor. Accordingly, the present inventors have further identified the utility in the methods and compositions of the present invention of compounds and agents which antagonise the function of further receptors which are activated by DNA. As such, the invention further extends to the use of compounds which inhibit the function of DNA receptors such as Nalp3/Cryopyrin, Pol III (DNA-dependent RNA polymerase III) or the RIG-1-like receptor (RLR) DAI, in order to provide an improved clinical treatment to prevent preterm labor and preterm birth. For example, the small molecule ML-60218 may be used to antagonise Pol III.

The term "epitope" as used herein relates to a portion of a macromolecule which is capable of being bound by a specific binding ligand, in this case, a portion of a polypeptide, in particular Toll-like Receptor 9. Epitopes may be defined from contiguous or non-contiguous sequences of amino acid residues comprised within a polypeptide sequence. The term "contiguous epitope" defines an epitope comprised of a linear series of amino acid residues within a polypeptide which define the epitope. A "non-contiguous epitope" is an epitope that is comprised of a series of amino acid residues that are non-linear in alignment, such that the residues are spaced or grouped in a non-continuous manner along the length of a polypeptide sequence. A non-continuous epitope can be a discontinuous epitope wherein the amino acid residues are grouped into 2 linear sequences, or alternatively the non-continuous epitope can be a discontinuous scattered epitope wherein the residues which contribute to the epitope are provided in 3 or more groups of linear amino acid sequences arranged along the length of the polypeptide.

Inhibitory Oligonucleotides

Methods for the synthesis of oligonucleotides for antisense applications are well known to the person skilled in the art and can be routinely accomplished (see for example, Agrawal, Methods in Molecular Biology, Protocols for Oligonucleotides and Analogs, 20:165-189, (1993), U.S. Pat. No. 5,149,798 and Antisense Research and Applications. Crooke, S. T. and Lebleu, B (Editors), CRC publishers. 1993).

Antibodies

An "antibody" is an immunoglobulin, whether natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd, and a bi-specific antibody.

In certain embodiments the antibody is selected from the group consisting of, but not limited to: a human, humanised, chimeric, synthetic, camelid, shark or in-vitro antibody, which has binding specificity to TLR9. In certain further embodiments, a binding fragment may be used, said binding fragment being derived from any of the aforementioned antibodies. In certain embodiments the antibody is an antibody binding fragment selected from the group consisting of a Fab, scFv, Fv, dAb, and fragment. In certain embodiments the antibody molecule comprises two complete heavy chains, and two complete light chains, or an antigen-binding fragment thereof. In certain embodiments, the antibody is of the isotype IgG, IgA, IgM. In embodiments where the antibody is of the isotype IgG, the antibody may be of the subtype IgG1, IgG2 or IgG3.

In certain embodiments, the antibody is an "isolated antibody", this meaning that the antibody is (1) free of at least some proteins with which it would normally be found, (2) is essentially free of other proteins from the same source, e.g., from the same species, (3) is expressed by a cell from a different species, or (4) does not occur in nature.

As antibodies can be modified in a number of ways, the term "antibody" should be construed as covering any binding member or substance having a binding domain with the required specificity. The antibody of the invention may be a monoclonal antibody, or a fragment, derivative, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in European Patent Application Publication Number EP 0,120,694 and European Patent Application Publication Number EP 0,125,023.

The constant region of the antibody may be of any suitable immunoglobulin subtype, however it is preferred that the antibody subtype is IgG1. However, in alternative embodiments, the subtype of the antibody may be of the class IgA, IgM, IgD and IgE where a human immunoglobulin molecule is used. Such an antibody may further belong to any subclass e.g. IgG1, IgG2a, IgG2b, IgG3 and IgG4.

Fragments of a whole antibody can perform the function of antigen binding. Examples of such binding fragments are; a Fab fragment comprising of the VL, VH, CL and CH1 antibody domains; an Fv fragment consisting of the VL and VH domains of a single antibody; a F(ab')2 fragments, a bivalent fragment comprising two linked Fab fragments; a single chain Fv molecule (scFv), wherein a VH domain and a VL domain are linked by a peptide linker which allows the two domains to associate to form an antigen binding site; or a bi-specific antibody, which may be multivalent or multispecific fragments constructed by gene fusion.

A fragment of an antibody or of a polypeptide for use in the present invention, for example, a fragment of a TLR9 specific antibody, generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

A "derivative" of such an antibody or polypeptide, or of a fragment of a TLR9 specific antibody means an antibody or polypeptide modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having TLR9 binding activity. Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

In certain embodiments, humanized antibodies are also provided. Humanized antibodies may be produced, for example, by the method of Winter as described in U.S. Pat. No. 5,585,089. A humanised antibody may be a modified antibody having the hypervariable region of a monoclonal antibody such as a TLR9 specific antibody and the constant region of a human antibody. Thus the binding member may comprise a human constant region. The variable region other than the hypervariable region may also be derived from the variable region of a human antibody and/or may also be derived from a monoclonal antibody such as a TLR9 specific antibody. In such case, the entire variable region may be derived from murine monoclonal antibody a TLR9 specific antibody and the antibody is said to be chimerized. Methods for making chimeric antibodies are known in the art. Such methods include, for example, those described in U.S. patents by Boss (Celltech) and by Cabilly (Genentech). See U.S. Pat. Nos. 4,816,397 and 4,816,567, respectively.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, European Patent Application No 0,184,187, GB Patent Application No. 2,188,638A or European Patent Application No. 0,239,400. A hybridoma or other cell producing an antibody may be subject to genetic mutation or other changes, which may or may not alter the binding specificity of antibodies produced.

In certain embodiments, where the TLR9 inhibitory compound or the TLR9 binding compound is an antibody, or an antibody binding fragment, wherein the antibody is administered to a subject in a therapeutically effective amount. In certain embodiments, the therapeutically effective amount comprises the antibody in a range chosen from 1 µg/kg to 20 mg/kg, 1 g/kg to 10 mg/kg, 1 µg/kg to 1 mg/kg, 10 µg/kg to 1 mg/kg, 10 µg/kg to 100 µg/kg and 500 µg/kg to 1 mg/kg.

Production of Antibodies

The antibodies provided by the present invention may be provided by a number of techniques. For example, a combinatorial screening technique such as a phage display-based biopanning assay may be used to in order to identify amino acid sequences which have binding specificity to the binding epitopes of the invention. Such phage display biopanning techniques involve the use of phage display libraries, which are utilised in methods which identify suitable epitope binding ligands in a procedure which mimics immune selection, through the display of antibody binding fragments on the surface of filamentous bacteria. Phage with specific binding activity are selected. The selected phage can thereafter be used in the production of chimeric, CDR-grafted, humanised or human antibodies.

In further embodiments, the antibody is a monoclonal antibody, which may be produced using any suitable method which produces antibody molecules by continuous cell lines in culture. Suitable methods will be well known to the person skilled in the art and include, for example, the method of Kohler and Milstein (Kohler et al. Nature, 256, 495-497. 1975). Chimeric antibodies or CDR-grafted antibodies are further provided within the scope of the present invention. In certain embodiments, the antibodies of the invention may be produced by the expression of recombinant DNA in host cell.

In certain embodiments, the monoclonal antibodies may be human antibodies, produced using transgenic animals, for example, transgenic mice, which have been genetically modified to delete or suppress the expression of endogenous murine immunoglobulin genes, with loci encoding for human heavy and light chains being expressed in preference, this resulting in the production of fully human antibodies.

In certain embodiments, the binding compound is a binding fragment which is derived from an antibody, for example, an antibody binding fragment, such as a Fab, F(ab')2, Fv or a single chain Fv (scFV).

In certain embodiments, the binding compound comprises a polyclonal antibody, a chimeric antibody, a synthesized or synthetic antibody, a fusion protein or fragment thereof, or a natural or synthetic chemical compound or a peptidomimetic. Methodologies for producing antibodies which have an affinity and binding specificity for the TLR9 epitope of the present invention are described hereinbefore.

The antibodies or antibody fragments of and for use in the present invention may also be generated wholly or partly by chemical synthesis. The antibodies can be readily prepared according to well-established, standard liquid or, preferably, solid-phase peptide synthesis methods, general descriptions of which are broadly available and are well known by the person skilled in the art. Further, they may be prepared in solution, by the liquid phase method or by any combination of solid-phase, liquid phase and solution chemistry.

Another convenient way of producing antibodies or antibody fragments suitable for use in the present invention is to express nucleic acid encoding them, by use of nucleic acid in an expression system.

Nucleic acid for use in accordance with the present invention may comprise DNA or RNA and may be wholly or partially synthetic. In a preferred aspect, nucleic acid for use in the invention codes for antibodies or antibody fragments of the invention as defined above. The skilled person will be able to determine substitutions, deletions and/or additions to such nucleic acids which will still provide an antibody or antibody fragment of the present invention.

Nucleic acid sequences encoding antibodies or antibody fragments for use with the present invention can be readily prepared by the skilled person using the information and references contained herein and techniques known in the art (for example, see Sambrook et al. (1989), and Ausubel et al, (1992)), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells, NS0 mouse myeloma cells. A common, preferred bacterial host is *E. coli*. The expression of antibodies and antibody fragments in prokaryotic cells such as *E. coli* is well established in the art. Expression in eukaryotic cells in culture is also available to those skilled in the art as an option for production of a binding member.

General techniques for the production of antibodies are well known to the person skilled in the field, with such methods being discussed in, for example, Kohler and Milstein (1975) Nature 256: 495-497; U.S. Pat. No. 4,376,110; Harlow and Lane, Antibodies: a Laboratory Manual, (1988) Cold Spring Harbor, the contents of which are incorporated herein by reference. Techniques for the preparation of recombinant antibody molecules are described in the above references and also in, for example, EP 0,623,679 and EP 0,368,684, which are incorporated herein by reference.

In certain embodiments of the invention, recombinant nucleic acids comprising an insert coding for a heavy chain variable domain and/or for a light chain variable domain of antibodies are employed. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

Recombinant DNA technology may be used to improve the functional properties of the antibodies of the invention. Thus, chimeric antibodies may be constructed in order to decrease the immunogenicity thereof. Moreover, the immunogenicity of the antibody may be minimised by altering the antibodies by CDR grafting. In order to reduce immunogenicity within a recipient, the invention may employ recombinant nucleic acids comprising an insert coding for a heavy chain variable domain of an antibody fused to a human constant domain. Likewise the invention concerns recombinant DNAs comprising an insert coding for a light chain variable domain of an antibody fused to a human constant domain kappa or lambda region.

Antibodies may moreover be generated by mutagenesis of antibody genes to produce 5 artificial repertoires of antibodies. This technique allows the preparation of antibody libraries. Antibody libraries are also available commercially. Hence, the present invention advantageously employs artificial repertoires of immunoglobulins, preferably artificial scFv repertoires, as an immunoglobulin source in order to identify binding molecules which have specificity for the epitope of the present invention.

Delivery of Antibodies

As Toll-like Receptor 9 is typically found within endosomes of cells, such as B-cells and macrophages, the antibodies or antibody fragments of the invention are preferably delivered in a manner which allows then to access the cell. The antibodies may be administered via microspheres, liposomes, other microparticulate delivery systems. The antibodies may be bi-specific antibodies which can bind specifically to a target cell and become internalised.

Antibody Selection Systems

Immunoglobulins which are able to act as TLR9 antagonists and which accordingly may be used in the methods of the invention can be identified using any technique known to the skilled person. Such immunoglobulins may be conveniently isolated from libraries comprising artificial repertoires of immunoglobulin polypeptides. A "repertoire" refers to a set of molecules generated by random, semi-random or directed variation of one or more template molecules, at the nucleic acid level, in order to provide a multiplicity of binding specificities. Methods for generating repertoires are well characterised in the art.

Any library selection system may be used in conjunction with the invention. Selection protocols for isolating desired members of large libraries are known in the art, as typified by phage display techniques. Such systems, in which diverse peptide sequences are displayed on the surface of filamentous bacteriophage, have proven useful for creating libraries of antibody fragments (and the nucleotide sequences that encode them) for the in-vitro selection and amplification of specific antibody fragments that bind a target antigen. The nucleotide sequences encoding the VH and VL regions are linked to gene fragments which encode leader signals that direct them to the periplasmic space of *E. coli* and as a result the resultant antibody fragments are displayed on the surface of the bacteriophage, typically as fusions to bacteriophage coat proteins (for example pill or pVIII). Alternatively, antibody fragments are displayed externally on lambda phage capsids (phage bodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straight forward.

Methods for the construction of bacteriophage antibody display libraries and lambda phage expression libraries are well known in the art (for example, McCafferty et al. (1990) Nature 348 552-554. One particularly advantageous approach has been the use of scFv phage-libraries (see for example Huston et al., 1988, Proc. Natl. Acad. Sci USA).

An alternative to the use of phage or other cloned libraries is to use nucleic acid, preferably RNA, derived from the B cells of an animal which has been immunised with the selected target, e.g. the TLR9 ligand binding epitope. Isolation of V-region and C-region mRNA permits antibody fragments, such as Fab or Fv, to be expressed intracellularly. Briefly, RNA is isolated from the B cells of an immunised animal, for example from the spleen of an immunised mouse or the circulating B cells of a llama, and PCR primers used to amplify VH and VL cDNA selectively from the RNA pool. The VH and VL sequences thus obtained are joined to make scFv antibodies. PCR primer sequences may be based on published VH and VL sequences.

Peptidomimetics

Peptide analogues, such as peptidomimetics or peptide mimetics are non-peptide compounds with properties representative of a template peptide. Such peptide analogues are typically developed using computerised molecular modelling. Peptidomimetics which are structurally similar to peptides which have affinity and binding specificity to the TLR9 ligand binding epitope may be used to mediate antagonism of TLR9.

Peptidomimetics are typically structurally similar to a template peptide, but have one or more peptide linkages replaced by an alternative linkage, by methods which are well known in the art. For example, a peptide which has a binding specificity for the TLR9 ligand binding site may be modified such that it comprises amide bond replacement, incorporation of non peptide moieties, or backbone cyclisation. Suitably if cysteine is present the thiol of this residue is capped to prevent damage of the free sulphate group. A peptide may further be modified from the natural sequence to protect the peptides from protease attack.

Suitably a peptide of and for use in the present invention may be further modified using at least one of C and/or N-terminal capping, and/or cysteine residue capping. Suitably, a peptide of and for use in the present invention may be capped at the N terminal residue with an acetyl group. Suitably, a peptide of and for use in the present invention may be capped at the C terminal with an amide group. Suitably, the thiol groups of cysteines are capped with acetamido methyl groups.

Expression, isolation and purification of TLR9 antagonist peptides or peptidomimetics may be accomplished by any suitable technique. A method for producing polypeptides comprises culturing host cells transformed with a recombinant expression vector encoding a polypeptide under conditions that promote expression of the polypeptide, then recovering the expressed polypeptides from the culture. The person skilled in the art will recognise that the procedure for purifying the expressed polypeptides will vary according to such factors as the type of host cells employed, and whether the polypeptide is intracellular, membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, avian, microbial, viral, bacterial, or insect gene. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired (*E. coli*) host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide during translation, but allows secretion of polypeptide from the cell.

Suitable host cells for expression of polypeptides include higher eukaryotic cells and yeast. Prokaryotic systems are also suitable. Mammalian cells, and in particular CHO cells are particularly preferred for use as host cells. Appropriate cloning and expression vectors for use with mammalian, prokaryotic, yeast, fungal and insect cellular hosts are described, for example, in Pouwels et al. Cloning Vectors: A Laboratory Manual, Elsevier, New York, (1986) (ISBN 0444904018).

Small Molecules

In various further aspects, the present invention relates to screening and assay methods for use in identifying small molecule compounds which antagonise TLR9 biological activity or expression. Certain further aspects extend to the compounds identified thereby, wherein said binding compounds have affinity and binding specificity for an epitope which, when bound, inhibits TLR9 functional activity.

A substance identified as an antagonist of TLR9 activation or signalling may be a peptide or may be non-peptide in nature, for example a peptidomimetic as described hereinbefore. However, non-peptide "small molecules" are often preferred for many in-vivo pharmaceutical uses. Accordingly, a mimetic or mimic of a TLR9 binding compound for use in the present invention may be designed for pharmaceutical uses.

The designing of mimetics to a known pharmaceutically active compound is a known approach to the development of pharmaceuticals based on a "lead" compound. This might be desirable where the active compound is difficult or expensive to synthesise, or where it is unsuitable for a particular method of administration. For example, peptides are not well suited as active agents for oral compositions and administration as they are degraded by proteases present in the alimentary canal.

Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, for example by substituting each amino acid residue in turn. These parts or residues constituting the active region of the compound are known as its "pharmacophore".

Once the pharmacophore has been determined, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can also be used in this modelling process.

In a variant of this approach, the three-dimensional structure of the TLR9 binding agent is modelled. This can be especially useful where the ligand and/or binding partner change conformation on binding, allowing the model to take account of the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in-vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in-vivo or clinical testing.

In certain embodiments, the mimetic binding compound may be a natural or synthetic chemical compound used in drug screening programmes. Extracts of plants which contain several characterised or uncharacterised components may also be used.

In yet further aspects, the invention extends to the use of combinatorial library technology (Schultz, J S (1996) Biotechnol. Prog. 12:729-743) which provides an efficient way of testing a potentially vast number of different substances for ability their ability to bind to an epitope or to modulate the activity of a ligand which binds to an epitope. Prior to, or as well as, being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide.

The amount of test substance or compound which may be added to an assay of the invention will normally be determined by trial and error depending upon the type of compound used. Typically, from about 0.01 to 100 nM concentrations of putative inhibitor compound may be used, for example from 0.1 to 10 nM. Greater concentrations may be used when a peptide is the test substance.

Combination Medicaments

As described hereinbefore, the present invention extends to combinational therapies wherein a composition comprising at least on TLR9 antagonist compound is administered in combination with at least one further therapeutic compound which serves to prevent preterm labor, for example a compound which is used in tocolytic therapy.

Typically the primary and secondary therapeutic compositions are given contemporaneously. In certain embodiments, the primary therapeutic composition (i.e. the binding compound which antagonises the functional activity of TLR9) and the secondary therapeutic compounds are administered simultaneously. In certain further embodiments, they are administered sequentially.

In certain embodiments, the combination therapy may comprise a TLR9 functional inhibitor that is co-administered to a subject along with at least one of: a cytokine inhibitor (such as, but not limited to an inhibitor of IL-6), and inhibitor of tumour necrosis factor, a growth factor inhibitor, an immunosuppressor, an anti-inflammatory, an enzymatic inhibitor, a metabolic inhibitor, a cytotoxic agent, a cytostatic agent, or any other agent which suppressed an immune response mediated by TLR9 following binding by fetal DNA.

A person of relevant skill in the field will recognise that the administration to a subject of a combination therapy can be advantageous in that it permits administration of a lower dose of therapeutic to a subject in order to achieve and associated therapeutically effective effect. The administration of a lower combined dose also results in the subject being exposed to a lower toxicity level derived from the administered compound. Furthermore, as the secondary therapeutic compounds which are administered as part of the combination therapy provided by the invention target different pathways, there is likely to be a synergistic improvement in the overall efficacy of the therapy. An improvement in efficacy would again result in the need for a lower dose to be administered and as such an associated reduction in toxicity.

In identifying and selecting suitable secondary therapeutic compounds for administration along with the TLR9 inhibitory compounds of the present invention, said secondary therapeutic compounds may be selected on the basis of such compounds modulating the immune response at a different stage of the inflammatory response which results in a proinflammatory response mediated by TLR9 following the binding of fetal DNA. Such secondary compounds may include, but are not limited to; soluble receptors, peptide inhibitor compound, small molecule, fusion proteins or ligands, antibodies, and cytokines which mediate an anti-inflammatory effect.

Administration

The TLR9 antagonist of the present invention may be administered alone but will preferably be administered as a pharmaceutical composition, which will generally comprise a suitable pharmaceutically acceptable excipient, diluent or carrier selected depending on the intended route of administration. Examples of suitable pharmaceutical carriers include; water, glycerol, ethanol and other GRAS reagents.

The monoclonal antibody or fusion protein of the present invention may be administered to a patient in need of treatment, typically a pregnant mother, via any suitable route. As detailed herein, it is preferred that the composition is administered parenterally by injection or infusion. Examples of preferred routes for parenteral administration include, but are not limited to; intravenous, intracardial, intraarterial, intraperitoneal, intramuscular, intracavity, subcutaneous, transmucosal, inhalation or transdermal. Routes of administration may further include topical and enteral, for example, mucosal (including pulmonary), oral, nasal, rectal.

Typically, the composition is deliverable as an injectable composition. For intravenous, intramuscular, intradermal or subcutaneous application, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

The composition is preferably administered to an individual in a "therapeutically effective amount", this being sufficient to show benefit to the individual to whom the composition is administered. The actual dose administered, and rate and time-course of administration, will depend on, and can be determined with due reference to, the nature and severity of the condition which is being treated, as well as factors such as the age, sex and weight of the patient to be treated and the route of administration. Further due consideration should be given to the properties of the composition, for example, its binding activity and in-vivo plasma life, the concentration of the fusion protein in the formulation, as well as the route, site and rate of delivery.

Dosage regimens can include a single administration of the composition of the invention, or multiple administrative doses of the composition. The compositions can further be administered sequentially or separately with other therapeutics and medicaments which are used for the treatment of the condition for which the fusion protein of the present invention is being administered to treat.

Examples of dosage regimens which can be administered to a subject can be selected from the group comprising, but not limited to; 1 µg/kg/day through to 20 mg/kg/day, 1 µg/kg/day through to 10 mg/kg/day, 10 µg/kg/day through to 1 mg/kg/day in instances where the TLR9 antagonist is a monoclonal antibody.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The nomenclature used to describe the polypeptide constituents of the fusion protein of the present invention follows the conventional practice wherein the amino group (N) is presented to the left and the carboxy group to the right of each amino acid residue.

The expression "amino acid" as used herein is intended to include both natural and synthetic amino acids, and both D and L amino acids. A synthetic amino acid also encompasses chemically modified amino acids, including, but not limited to salts, and amino acid derivatives such as amides. Amino acids present within the polypeptides of the present invention can be modified by methylation, amidation, acetylation or substitution with other chemical groups which can change the circulating half life without adversely affecting their biological activity.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived Furthermore the term "fusion protein" as used herein can also be taken to mean a fusion polypeptide, fusion peptide or the like, or may also be referred to as an immunoconjugate. The term "fusion protein" refers to a molecule in which two or more subunit molecules, typically polypeptides, are covalently or non-covalently linked.

As used herein, a Toll-like Receptor 9 antagonist (TLR9 antagonist) is a compound which inhibits, suppresses, blocks or downregulates Toll-like Receptor 9 activation, for example by preventing the binding to Toll-like Receptor 9 of an activating ligand, such as fetal DNA. The TLR9 antagonist may inhibit, suppress, block or downregulate intracellular signalling mediated by Toll-like Receptor 9, such as the TLR/IL-1R signalling pathway, following activation of TLR9 by a ligand agonist, such as fetal DNA. In particular antagonists of Toll-like Receptor 9 signaling are molecules that intervene in the different steps of the Toll-like Receptor 9 activation and signaling, including Toll-like Receptor 9 binding, Toll-like Receptor 9 relocalization, MAP kinase activity and transcription factor activation. A Toll-like Receptor 9 antagonist may further inhibit the expression of Toll-like Receptor 9. Hence, typically the Toll-like Receptor 9 antagonist is an agent acts as a Toll-like Receptor 9 ligand which binds to Toll-like Receptor 9 but which, unlike an agonist, blocks the signalling cascade mediated by Toll-like Receptor 9. Such antagonistic agents can therefore function as Toll-like Receptor 9 signalling inhibitors.

As used herein, the term "therapeutically effective amount" means the amount of an agent, binding compound, small molecule, fusion protein or peptidomimetic of the invention which is required to suppress TLR9-mediated inflammation which is causative of preterm labor. Similarly, as used herein, the term "prophylactically effective amount" relates to the amount of a composition which is required to prevent the initial onset, progression or recurrence of TLR9-mediated inflammation which is causative of preterm labor in a pregnant mother.

As used herein, the term "subject" refers to an animal, preferably a mammal and in particular a human, typically a pregnant mother. In a particular embodiment, the subject is a mammal, in particular a human. The term "subject" is interchangeable with the term "patient" as used herein.

EXAMPLES

Example 1

Fetal DNA Induces I-kappa-B Degradation and p38 Phosphorylation

Namalwa B cells were exposed to fetal DNA. This example assesses whether fetal DNA induces I-kappa-B degradation and p38 phosphorylation in Namalwa B cells in response to exposure of that TLR9 expressing cell line to fetal DNA, and compares any activation to that induced by exposure of the Namalwa B cells to activation with the TLR9 agonist CpG DNA.

Methods

Namalwa cells, a B-cell line isolated from Burkitt's lymphoma obtained from a 3 year old African female, which have been documented to express TLR-9, were used for the initial studies. Namalwa cells were cultured at a concentration of $2.0 \times 10^6$ cells/ml. The cells were first tested for the presence of TLR-9 in the supernatant and immunoblotted for TLR-9. Namalwa cells, which are a B-cell line from Burkitts lymphoma, were chosen as a model cell line since these cells demonstrate a high level of TLR-9 expression.

For the time course studies, Namalwa cells cultured at a concentration of $2.0 \times 10^6$ cells/ml were stimulated for various times using fetal DNA isolated from a 22 week female fetus at a concentration of 3 µg/ml. The functional control was a CpG containing DNA oligonucleotide (CpG) at a concentration of 3 µg/ml which was used to stimulate Namalwa cells in the same time course. Finally, female adult DNA isolated from blood at a concentration of 3 µg/ml was also used to stimulate Namalwa cells. Iκβ degradation was measured by immunoblotting.

The Anti-Iκβ-α antibody was a gift from Prof. R. Hay (University of Dundee, Dundee, U.K.), The polyclonal phosphor-p38 antibody was obtained from Cell Signaling Technology. The anti-TLR 9 antibody was purchased from Imgenex. The anti-mouse IgG (whole molecule) peroxidise conjugate and the anti-rabbit IgG (whole molecule) peroxidise conjugate antibodies were all purchased from Jackson ImmunoResearch Laboratories. Human CpG-b was purchased from Invivogen. IL-6 ELISAs were obtained from R&D Systems. Fetal DNA and adult DNA was purchased from Biochain. The Namalwa cells were a gift from Opsona Therapeutics (Dublin, Ireland) and the murine bone-marrow derived macrophages were a gift from Dr. Claire Bryant (University of Cambridge, U.K.).

Results

Fetal DNA dose-dependently in (µg/ml) induces IkB degradation from 0.1 µg/ml fetal DNA concentration, at an incubation time of 15 minutes on Namalwa cells at $2.0 \times 10^7$ cells/ml using immunoblotting protocols. Using immunoblotting techniques, fetal DNA at a concentration of 1.5 µg/ml induces p38 phosphorylation when stimulating Namalwa B cells at $2.0 \times 10^7$ cells/ml over time in minutes.

In FIG. 1(a) Namalwa cells were stimulated with fetal DNA (fDNA) causing I-kappa-B degradation over time (in minutes) compared with that seen with the CpG-DNA control. In FIG. 1(b) Phosphorylation of p38 occurs when stimulating Namalwa cells with fetal DNA over time. In FIG. 1(c) dose-dependent fetal DNA induces IkB degradation from 0.1 microgram/ml fetal DNA concentration, at an incubation time of 15 minutes.

The results shown in FIG. 1 indicate that fetal DNA can (a) activate I-kappaB degradation in a time-course dependent manner, (b) that fetal DNA activates p38 MAP kinase, and (c) that fetal DNA cause I-kappaB degradation in a dose dependent manner. All of these responses are in the TLR9 expressing B cell line, Namalwa. The observed stimulatory effect of fetal DNA is more potent than that seem with the TLR9 ligand agonist CpG DNA.

Example 2

Figure 2A:
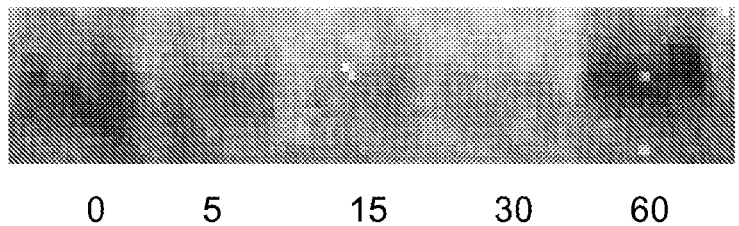
FIGS. 2A, 2B and 2C show that fetal DNA induces I-kappa-B degradation in Namalwa B cells.
Figure 2A:
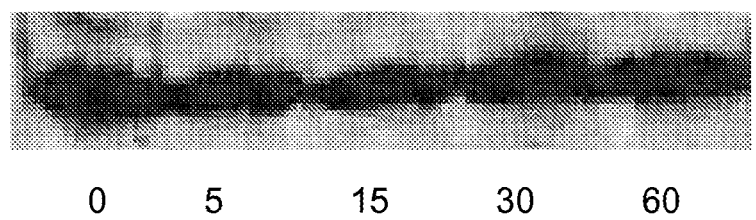
Figure 2B:
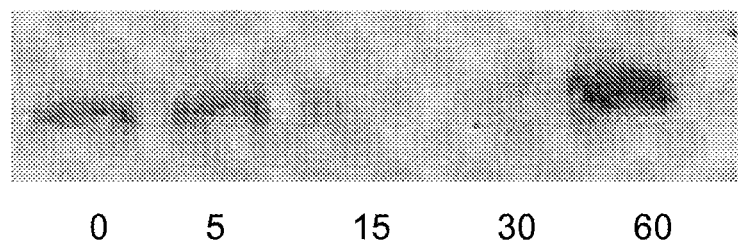
Figure 2B:
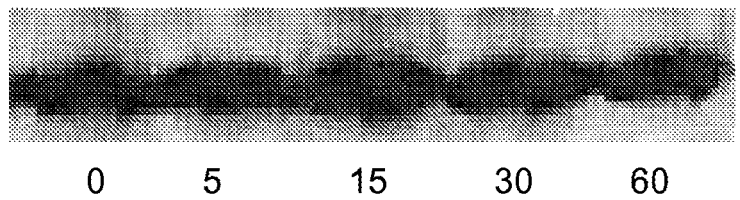
Figure 2C:
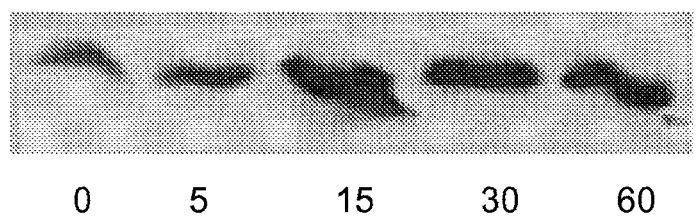
Figure 2C:
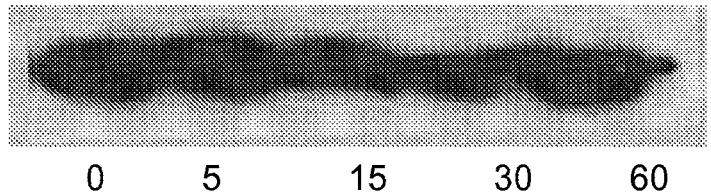
Figure 3A:
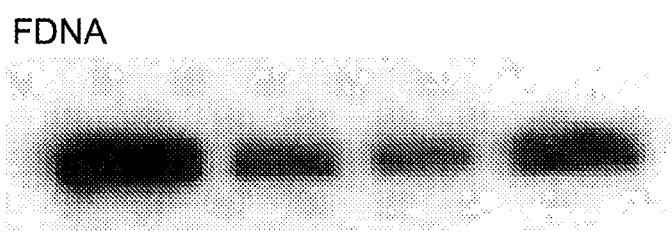
FIG. 3A shows that PBMCs stimulated with fetal DNA led to IkB degradation.
Figure 3A:
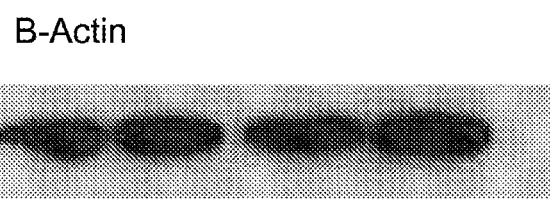
Figure 3B:
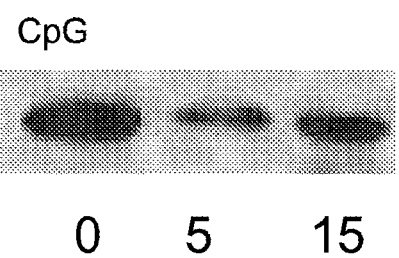
FIG. 3B shows that stimulation of PBMCs with a TLR9 agonist, CpG, at the same concentration also induced comparable IkB degradation.
Figure 3B:
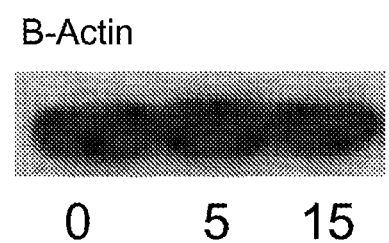
Figure 3C:
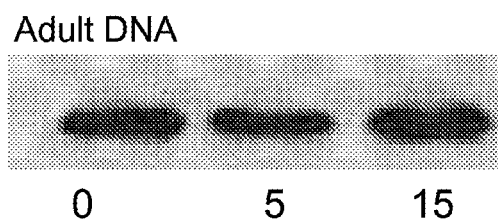
FIG. 3C shows stimulation of the PBMCs with Adult DNA did not induce IkB degradation in PBMCs when stimulating over the same time period.
Figure 3C:
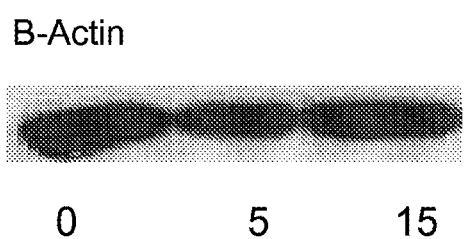

Fetal DNA and the Toll-Like Receptor 9 Agonist CpG DNA Mediate 1-Kappa-B degradation Namalwa B cells as described in Example 1 were exposed to fetal DNA (FDNA) (FIG. 2A), a TLR9 agonist CpG (FIG. 2B) and adult DNA (FIG. 2C). It is shown that fetal DNA induces IkB (I-kappa-B) degradation in Namalwa B cells (FIG. 2A).

Specifically, Namalwa cells at a concentration of $2.0 \times 10^7$ cells/ml were stimulated for various times (in minutes) with fetal DNA (fDNA, FDNA) at a concentration of 3 µg/ml, a CpG containing DNA oligonucleotide (CpG) (3 µg/ml) or adult DNA (3 µg/ml). IkB (I-kappa-B) degradation was measured by immunoblotting.

Results

Both fetal DNA and CpG DNA, but not adult DNA concentration induced I-kappa-B degradation. Hence, it can be concluded that both fetal DNA and the TLR9 agonist CpG DNA activate Toll-like Receptor 9, but that adult DNA does not act as a Toll-like Receptor 9 agonist.

Example 3

Fetal DNA and the Toll-like Receptor 9 Agonist CpG DNA Mediate I-kappa-B Degradation in PBMCs Confirmation of the findings of Examples 1 and 2 was sought by assessing IkB degradation in a peripheral blood mononuclear cell (PBMC) model.

PBMCs from female donors were set up at a concentration of $2.5 \times 10^6$ cells/ml and incubated for 24 hours. They were then stimulated with fetal DNA, adult DNA and human CpG (a TLR9 agonist) at a concentration of 1.5 µg/ml, at various times in accordance with the method used in Examples 1 and 2 in respect of stimulating the Namalwa cells. IkB degradation was measured by immunoblotting. Beta actin was used as a control.

Measurement of the cytokine IL-6 induction was also performed in the PBMC population as described above.

Results

FIG. 3 shows that fetal DNA induces I-kappaB degradation in peripheral blood mononuclear cells (PBMCs). FIG. 3A shows that PBMCs stimulated with fetal DNA led to IkB degradation. FIG. 3B shows that stimulation of PBMCs with a TLR9 agonist, CpG, at the same concentration also induced comparable IkB degradation. However, stimulation of the PBMCs with Adult DNA (FIG. 3C) did not induce IkB degradation in PBMCs when stimulating over the same time period.

Example 4

Fetal DNA Induces I-kappa-B Degradation and p38 Phosphorylation

Figure 4A:
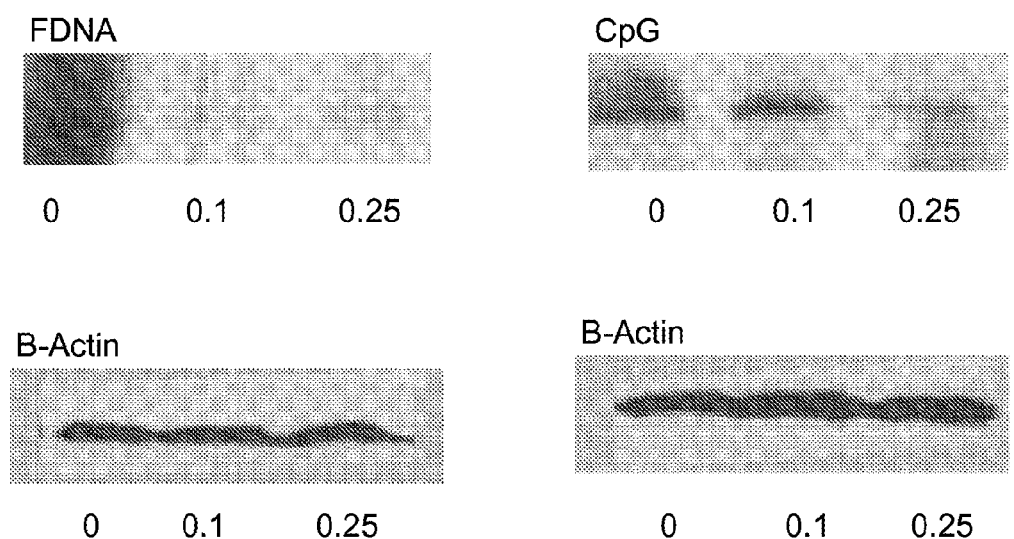
FIG. 4A shows that fetal DNA administered in a dose-dependent manner (in [mu]g/ml) induces IkB degradation from 0.1 [mu]g/ml FDNA (fetal DNA) concentration, at an incubation time of 15 minutes on Namalwa B cells at 2.0×10<7> cells/ml using immunoblotting protocols.

In FIG. 4(A), fetal DNA administered in a dose-dependent manner (in µg/ml) induces IkB degradation from 0.1 µg/ml FDNA (fetal DNA) concentration, at an incubation time of 15 minutes on Namalwa B cells at $2.0 \times 10^7$ cells/ml using immunoblotting protocols.

Figure 4B:
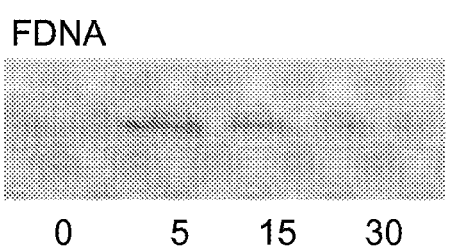
FIG. 4B shows that, by using immunoblotting techniques, FDNA at 1.5 micrograms/ml concentration induces p38 phosphorylation when stimulating Namalwa cells at 2.0×10<7> cells/ml over time in minutes.
Figure 4B:
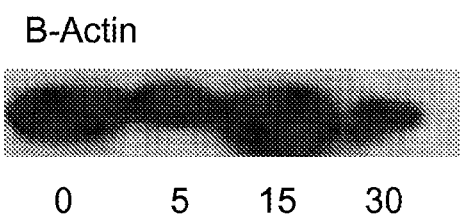

In FIG. 4(B) it is shown using immunoblotting techniques, that FDNA at 1.5 micrograms/ml concentration induces p38 phosphorylation when stimulating Namalwa cells at $2.0 \times 10^7$ cells/ml over time in minutes.

Example 5

Inhibition of Fetal DNA Mediated I-kappaB Function by TLR9 Inhibitors

This example considers whether an inhibitory ODN (oligonucleotide) which is known to inhibit TLR9 function, and the Toll-like Receptor 9 antagonist chloroquine inhibit induction of I-kappa-B degradation by fetal DNA.
Method
Inhibition of Toll-like Receptor 9 was carried out using the Toll-like Receptor 9 antagonist cholorquine and a synthetic inhibitory oligodinucleotide (TTAGGG) which was obtained from InvivoGen. Cholorquine was used to pre-treat Namalwa cells at $2.0 \times 10^6$ cells/ml at an optimal concentration of 75 microM. The recommended concentration from package inserts was to use a 10-100 microM concentration. The system was optimized at 75 microM. The same fetal DNA (3.0 µg/ml) was then used to stimulate cells over time in minutes as described above.

Namalwa cells ($2.0 \times 10^7$ cells/ml) were also incubated with synthetic inhibitory TLR-9 oligonucleotide (ODN+) at an 8:1 ratio of oligodinucleotide (ODN) to ligand. The package insert recommended a 1-10:1 ratio of inhibitory oligodinucleotide (ODN) to stimulatory oligodinucleotide (ODN). The system was optimized at an 8:1 ratio. This was followed by stimulation with the same purchased fetal DNA at 3.0 µg/ml using the method described hereinbefore.

Figure 5:
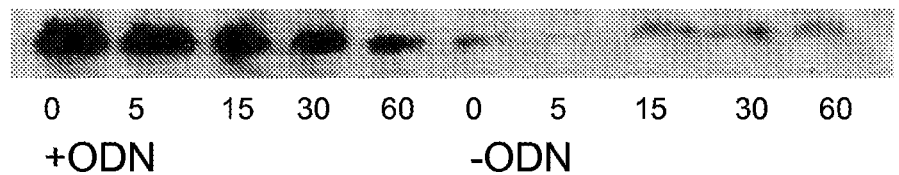
FIG. 5A shows that an inhibitory oligonucleotide, which is known to inhibit TLR9, can limit the activation of 1-kappaB degradation by fetal DNA.
FIG. 5B shows that chloroquine (which has also been shown to block TLR9 signaling) can also inhibit this response.
Figure 5:
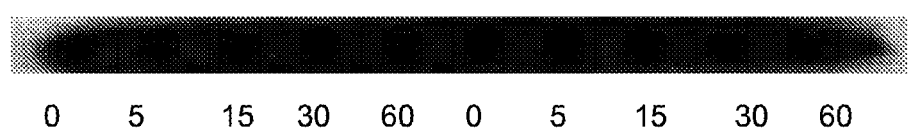
Figure 5:
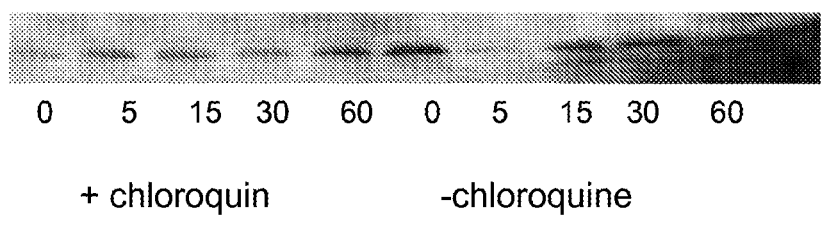
Figure 5:
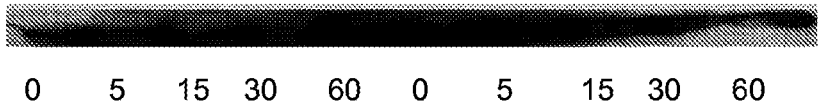
Figure 6A:
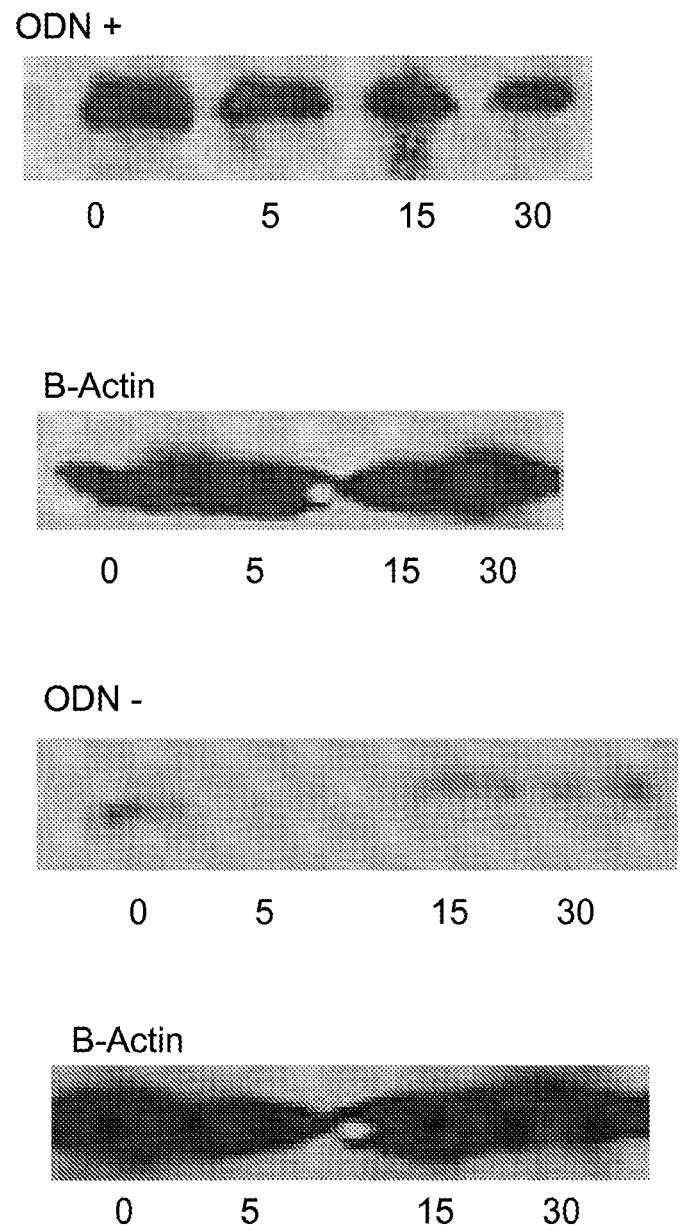
FIGS. 6A and B further show that an inhibitory oligodinucleotide (ODN) and chloroquine inhibit induction of 1-kappa-B degradation by fetal DNA. Chloroquine blocked 1-kappa-B degradation in the pre-treated cells compared with the untreated Beta actin controls (FIG. 6B).

In FIGS. 5A and 6A Namalwa cells ($2.0 \times 10^7$ cells/ml) were incubated with the inhibitory TLR-9 oligonucleotide (ODN+) in an 8:1 ratio of ODN to ligand. This was followed by stimulation with fetal DNA at a concentration of 3.0 µg/ml. The inhibitory oligodinucleotide (ODN) blocked I-kappa-B degradation over time in minutes (compare left and right hand panels).

Figure 6B:
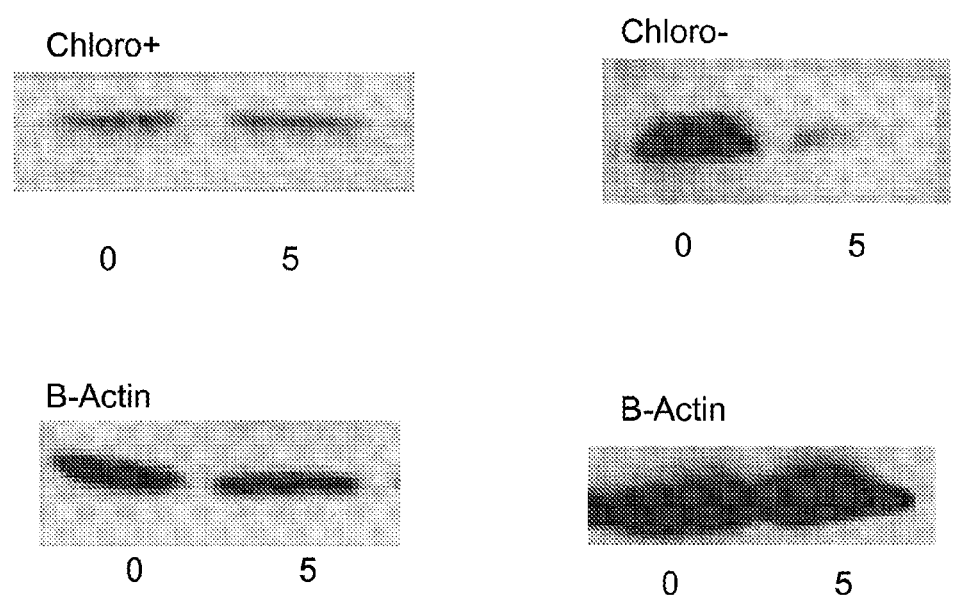
FIG. 6 shows that an inhibitory oligodinucleotide (ODN) and chloroquine inhibit induction of 1-kappa-B degradation by fetal DNA.

In FIGS. 5B and 6B, the TLR9 antagonist cholorquine was used to pre-treat Namalwa cells at $2.0 \times 10^7$ cells/ml at a concentration of 75 µM. Fetal DNA (3.0 microg/ml) was then used to stimulate cells over time in minutes.
Results
In FIG. 5A Namalwa B cells were incubated with inhibitory TLR-9 oligonucleotide (ODN) followed by fetal DNA for the times shown and I-kappaB degradation was assayed. ODN Blocks I-kappa-B degradation. In FIG. 5A it is shown that an inhibitory oligonucleotide, which is known to inhibit TLR9, can limit the activation of I-kappaB degradation by fetal DNA. In FIG. 5B it is shown that chloroquine (which has also been shown to block TLR9 signaling) can also inhibit this response.

The results of these experiments therefore show initial evidence for TLR9 involvement in the pro-inflammatory effect of fetal DNA.

In FIG. 5B Namalwa B cells were pre-treated with chloroquine (which inhibits TLR9) and then incubated with fetal DNA for the indicated times (in minutes). Induction of I-kappa-B degradation was inhibited.

FIGS. 6A and B further show that an inhibitory oligodinucleotide (ODN) and chloroquine inhibit induction of I-kappa-B degradation by fetal DNA. Chloroquine blocked I-kappa-B degradation in the pre-treated cells compared with the untreated Beta actin controls (FIG. 6B).

Example 6

Specificity of Fetal DNA in I-kappaB Degradation

Figure 7:
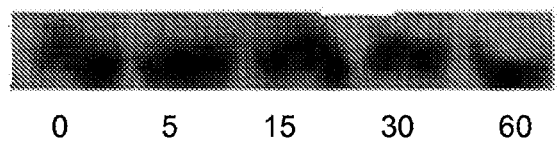
FIG. 7 shows that adult DNA does not cause 1-kappaB degradation, pointing to specificity in the effect of the fetal DNA.
Figure 7:
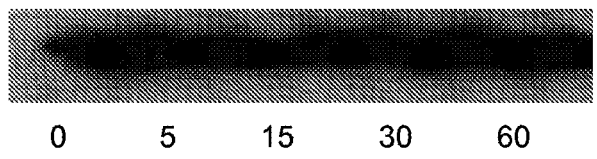

In FIG. 7 it is shown that adult DNA does not cause I-kappaB degradation, pointing to specificity in the effect of the fetal DNA.

Adult DNA does not activated I-kappaB (IkB) degradation. In FIG. 7A adult DNA from the peripheral blood of a female subject does not result in IkB degradation when used to stimulate Namalwa cells, when performed in a time course in minutes (FIG. 7A). FIG. 7(b) shows a B-actin control for the same experiment.

Example 7

Adult DNA and Fetal DNA Mediated IL-6 Cytokine Expression

This example was used to determine whether the expression of IL-6 resulted from stimulation of fetal DNA only, or also from adult DNA.
Method
To measure the concentration of IL-6, Namalwa cells at $2.0 \times 10^6$ cells/ml concentration were stimulated with fetal DNA (0.5 µg/ml, 1 µg/ml and 2 µg/ml) sourced from the umbilical cord of a 22 week old fetus or adult DNA sourced from PBMCs from an adult female for 18 hours, and CpG for various times. IL-6 production levels (µg/ml) were measured in the supernatants using standard ELISA kits.

Figure 8:
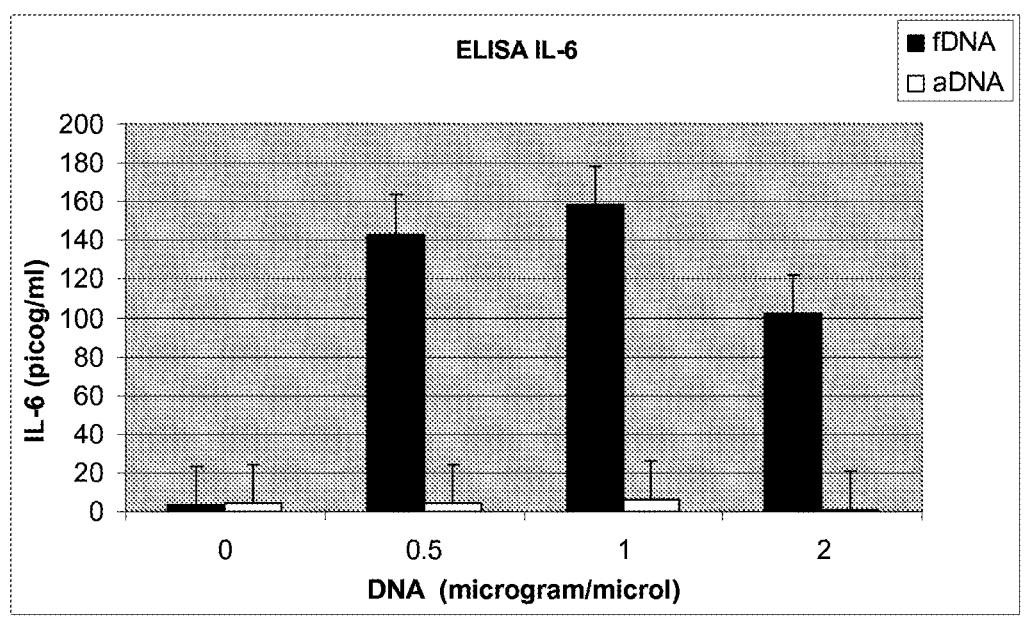
FIG. 8 shows that fetal but not adult DNA induces IL-6 cytokine expression in Namalwa cells.

Namalwa cells at $2.0 \times 10^6$ cells/ml were stimulated with FDNA (0.5 µg/ml, 1 µg/ml and 2 µg/ml) sourced from the umbilical cord of a 22 week old fetus or adult DNA sourced from PBMCs from an adult female for 18 hours. IL-6 production levels (µg/ml) were measured by ELISA in the supernatants.
Results
The results are shown in FIG. 8. Fetal but not adult DNA induces IL-6 cytokine expression in Namalwa cells, the expression of IL-6 being another marker of inflammation. Data shown is mean+/−s.d. from triplicate determinations.

Example 8

IL-6 Production by PBMCs

Figure 9:
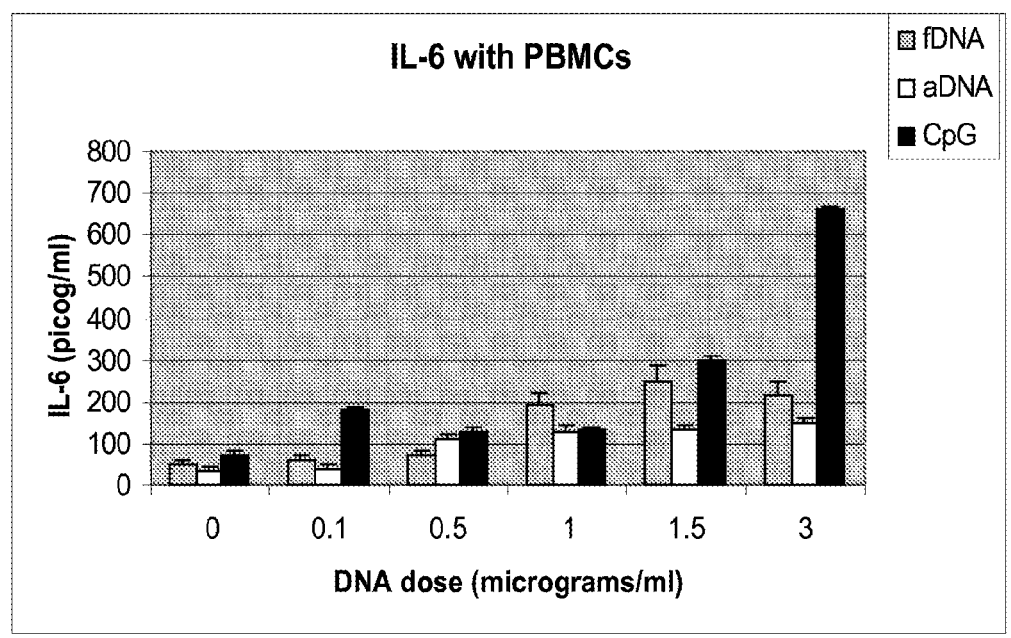
FIG. 9 shows that fetal DNA is much more potent inducer of IL-6 in peripheral blood mononuclear cells, with CpG DNA having the strongest effect.

Method
Human peripheral blood mononuclear cells (PBMCs) at $2.0 \times 10^6$ cells/ml from an adult female were stimulated at differing concentrations in ug/ml of fetal DNA, Adult DNA, and CpG for 16 hours. IL-6 was then measured by ELISA.
Results
FIG. 9 shows the results, wherein fetal DNA and CpG stimulated IL-6 production in a dose responsive manner, whereas adult DNA did not. Data shown is mean+/−s.d from triplicate determinations. It can therefore be concluded from these results that fetal DNA is much more potent inducer of IL-6 in peripheral blood mononuclear cells, with CpG DNA having the strongest effect. IL-6 levels were measured in the supernatants by ELISA

Example 9

IL-6 Expression in TLR9 Expressing and TLR9 Deficient Macrophages

TLR9-deficient or wild-type bone marrow derived macrophages (BMDM) were set up at a concentration of $2.0 \times 10^6$ cells/ml. The cells were then incubated with differing concentrations of fetal DNA (in μg/ml) for 18 hours. IL-6 concentrations in supernatants were then measured by standardised ELISA kits.

Figure 10:
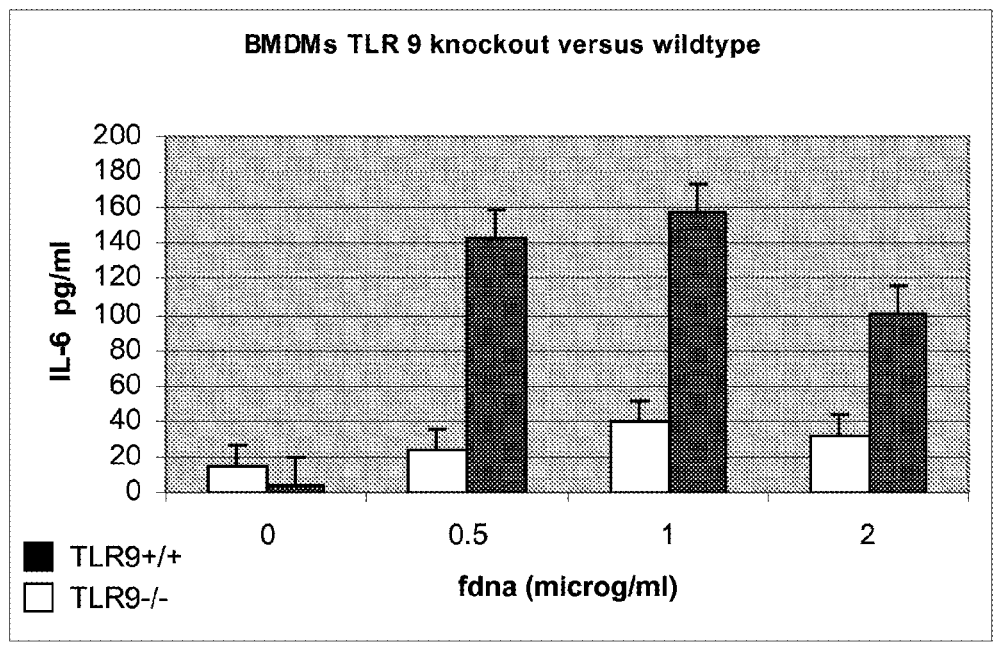
FIG. 10 shows that fetal DNA induces IL-6 expression in wild-type (TLR9+/+), but not TLR9-deficient (TLR9−/−) bone marrow-derived macrophages.

The results are shown in FIG. 10. In FIG. 10 it is shown that fetal DNA induces IL-6 expression in wild-type, but not TLR9-deficient (TLR9−/−) bone marrow-derived macrophages (BMDMs). The knockout cells did not respond compared with wildtypes. Results shown are mean+/−s.d. from triplicate determinations.

The results shown that TLR9-deficient bone marrow-derived macrophages (BMDMs) do not respond to fetal DNA in terms of IL-6 induction.

SUMMARY

In conclusion, the results of the above experiments show that (i) fetal DNA added to the Namalwa B cell line or PMBCs rapidly activates NF-kappaB and p38, and also induces production of the pro-inflammatory cytokine IL-6. It is also shown that the effects of fetal DNA were more potent that either synthetic CpG containing oligonucleotides, or adult DNA. Furthermore, inhibitory oligodinucleotides (ODN) and the TLR9 antagonist chloroquine are shown to inhibit TLR9 signaling, and both blocked the effect of fetal DNA on I-kappaB degradation. Fetal DNA mediated IL-6 cytokine induction is significantly reduced in TLR9-deficient bone marrow-derived macrophages, while TLR-9 senses fetal DNA and facilitates an inflammatory reaction. The results have therefore surprisingly identified a new ligand for TLR-9 that is, fetal DNA. Fetal DNA was found to be stronger than adult DNA at driving 10 degradation and inducing production of IL-6. This is likely to be due to the higher CPG content. The effect was TLR dependant since it was blocked by chloroquine and an inhibitory oligodinucleotide (ODN) and was abolished in TLR-9 deficient cells.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A method for reducing the incidence of onset of premature labor and/or preterm birth caused by fetal DNA induced inflammatory response, the method comprising the steps of:
providing a therapeutically effective amount of an agent which is an antagonist of Toll-like Receptor 9 (TLR9) biological activity and intracellular signaling, wherein the agent is chloroquine, and
administering the agent to a pregnant female subject in need of such treatment, wherein administration of the agent blocks TLR9-meditated fetal DNA induced inflammatory response.

2. The method as claimed in claim 1 further comprising the step of administering a therapeutically effective amount of at least one secondary therapeutic compound, said secondary therapeutic compound being an immunosuppressant compound.

3. The method as claimed in claim 2 wherein the secondary therapeutic compound is an immunosuppressant selected from the group consisting of: a glucocorticoid, a cytostatic, an anti-metabolite, an anti-CD2 antibody or related binding fragment, an anti-CD20 antibody, an anti-TNF-alpha antibody, cyclosporine, tacrolimus, sirolimus and FTY720.

4. The method as claimed in claim 1 further comprising the step of administering at least one compound used in tocolytic therapy.

5. The method as claimed in claim 4 wherein the at least one compound used in tocolytic therapy is selected from the group consisting of ritodrine, terbutaline, hexoprenaline, magnesium sulphate, indomethacin and nifedipine.

* * * * *

SEQUENCE LISTING

```
<160> NUMBER OF SEQ ID NOS: 1

<210> SEQ ID NO 1
<211> LENGTH: 972
<212> TYPE: PRT
<213> ORGANISM: Homo sapiens

<400> SEQUENCE: 1

Met Gly Phe Cys Arg Ser Ala Leu His Pro Leu Ser Leu Leu Val Gln
1               5                   10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
    130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
```

```
                180                 185                 190
Gly Ala Leu Leu Gly Leu Gly Ser Leu Thr His Leu Ser Leu Lys Tyr
            195                 200                 205
Asn Asn Leu Thr Val Val Pro Arg Asn Leu Pro Ser Ser Leu Glu Tyr
        210                 215                 220
Leu Leu Leu Ser Tyr Asn Arg Ile Val Lys Leu Ala Pro Glu Asp Leu
225                 230                 235                 240
Ala Asn Leu Thr Ala Leu Arg Val Leu Asp Val Gly Gly Asn Cys Arg
                245                 250                 255
Arg Cys Asp His Ala Pro Asn Pro Cys Met Glu Cys Pro Arg His Phe
            260                 265                 270
Pro Gln Leu His Pro Asp Thr Phe Ser His Leu Ser Arg Leu Glu Gly
        275                 280                 285
Leu Val Leu Lys Asp Ser Ser Leu Ser Trp Leu Asn Ala Ser Trp Phe
    290                 295                 300
Arg Gly Leu Gly Asn Leu Arg Val Leu Asp Leu Ser Glu Asn Phe Leu
305                 310                 315                 320
Tyr Lys Cys Ile Thr Lys Thr Lys Ala Leu Gln Gly Leu Thr Gln Leu
                325                 330                 335
Arg Lys Leu Asn Leu Ser Phe Asn Tyr Gln Lys Arg Val Ser Phe Ala
            340                 345                 350
His Leu Ser Leu Ala Pro Ser Phe Gly Ser Leu Val Ala Leu Lys Glu
        355                 360                 365
Leu Asp Met His Gly Ile Phe Phe Arg Ser Leu Asp Glu Thr Thr Leu
    370                 375                 380
Arg Pro Leu Ala Arg Leu Pro Met Leu Gln Thr Leu Arg Leu Gln Met
385                 390                 395                 400
Asn Phe Ile Asn Gln Ala Gln Leu Gly Ile Phe Arg Ala Phe Pro Gly
                405                 410                 415
Leu Arg Tyr Val Asp Leu Ser Asp Asn Arg Ile Ser Gly Ala Ser Glu
            420                 425                 430
Leu Thr Ala Thr Met Gly Glu Ala Asp Gly Gly Glu Lys Val Trp Leu
        435                 440                 445
Gln Pro Gly Asp Leu Ala Pro Ala Pro Val Asp Thr Pro Ser Ser Glu
    450                 455                 460
Asp Phe Arg Pro Asn Cys Ser Thr Leu Asn Phe Thr Leu Asp Leu Ser
465                 470                 475                 480
Arg Asn Asn Leu Val Thr Val Gln Pro Glu Met Phe Ala Gln Leu Ser
                485                 490                 495
His Leu Gln Cys Leu Arg Leu Ser His Asn Cys Ile Ser Gln Ala Val
            500                 505                 510
Asn Gly Ser Gln Phe Leu Pro Leu Thr Gly Leu Gln Val Leu Asp Leu
        515                 520                 525
Ser His Asn Lys Leu Asp Leu Tyr His Glu His Ser Phe Thr Glu Leu
    530                 535                 540
Pro Arg Leu Glu Ala Leu Asp Leu Ser Tyr Asn Ser Gln Pro Phe Gly
545                 550                 555                 560
Met Gln Gly Val Gly His Asn Phe Ser Phe Val Ala His Leu Arg Thr
                565                 570                 575
Leu Arg His Leu Ser Leu Ala His Asn Asn Ile His Ser Gln Val Ser
            580                 585                 590
Gln Gln Leu Cys Ser Thr Ser Leu Arg Ala Leu Asp Phe Ser Gly Asn
        595                 600                 605
```

```
Ala Leu Gly His Met Trp Ala Glu Gly Asp Leu Tyr Leu His Phe Phe
    610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
            660                 665                 670

Leu His Phe Leu Pro Lys Leu Glu Val Leu Asp Leu Ala Gly Asn Gln
        675                 680                 685

Leu Lys Ala Leu Thr Asn Gly Ser Leu Pro Ala Gly Thr Arg Leu Arg
    690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
        755                 760                 765

Ala Phe Met Asp Phe Leu Leu Glu Val Gln Ala Ala Val Pro Gly Leu
    770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Leu Ala Val Ala Leu Gly Leu Gly Val
            820                 825                 830

Pro Met Leu His His Leu Cys Gly Trp Asp Leu Trp Tyr Cys Phe His
    835                 840                 845

Leu Cys Leu Ala Trp Leu Pro Trp Arg Gly Arg Gln Ser Gly Arg Asp
850                 855                 860

Glu Asp Ala Leu Pro Tyr Asp Ala Phe Val Val Phe Asp Lys Thr Gln
                865                 870                 875                 880

Ser Ala Val Ala Asp Trp Val Tyr Asn Glu Leu Arg Gly Gln Leu Glu
            885                 890                 895

Glu Cys Arg Gly Asp Arg Lys Asp Val Val Leu Val Ile Leu Ser
        900                 905                 910

Pro Asp Gly Arg Arg Ser Arg Tyr Val Arg Leu Arg Gln Arg Leu Cys
    915                 920                 925

Arg Gln Ser Val Leu Leu Trp Pro His Gln Pro Ser Gly Gln Arg Ser
930                 935                 940

Phe Trp Ala Gln Leu Gly Met Ala Leu Thr Arg Asp Asn His His Phe
945                 950                 955                 960

Tyr Asn Arg Asn Phe Cys Gln Gly Pro Thr Ala Glu
                965                 970
```